(12) United States Patent
Liang et al.

(10) Patent No.: US 12,384,771 B2
(45) Date of Patent: Aug. 12, 2025

(54) PLEUROMUTILIN DERIVATIVE CONTAINING THIAZOLE-PYRIDINE BENZYL QUATERNARY AMMONIUM SALT SIDE CHAIN AND PREPARATION METHOD AND USE THEREOF

(71) Applicant: SHAANXI UNIVERSITY OF SCIENCE AND TECHNOLOGY, Xi'an (CN)

(72) Inventors: Chenguan Liang, Xi'an (CN); Kairui Kang, Xi'an (CN); Changhua Ke, Xi'an (CN); Yanzi Wang, Xi'an (CN); Yuting Liu, Xi'an (CN); Xiuding Yang, Xi'an (CN); Ying Zhou, Xi'an (CN); Jiaxuan Li, Xi'an (CN)

(73) Assignee: SHAANXI UNIVERSITY OF SCIENCE AND TECHNOLOGY, Shaanxi (CN)

( * ) Notice: Subject to any disclaimer, the term of this patent is extended or adjusted under 35 U.S.C. 154(b) by 158 days.

(21) Appl. No.: 18/126,355

(22) Filed: Mar. 24, 2023

(65) Prior Publication Data
US 2023/0312546 A1    Oct. 5, 2023

(30) Foreign Application Priority Data

Mar. 29, 2022 (CN) .......................... 202210320742.7

(51) Int. Cl.
*A61P 31/00* (2006.01)
*A61P 31/04* (2006.01)
*C07D 417/04* (2006.01)

(52) U.S. Cl.
CPC ............ *C07D 417/04* (2013.01); *A61P 31/04* (2018.01)

(58) Field of Classification Search
None
See application file for complete search history.

(56) References Cited

FOREIGN PATENT DOCUMENTS

| CN | 106008395 A | 10/2016 |
|----|-------------|---------|
| CN | 110818648 A | 2/2020 |
| CN | 111170911 A | 5/2020 |
| CN | 111689914 A | 9/2020 |
| CN | 113149929 A | 7/2021 |
| JP | 2005529088 A | 9/2005 |

OTHER PUBLICATIONS

Xia, Juan, et al., Journal of Medicinal Chemistry (2023), 66(7), 5061-5078 (Year: 2023).*
Xia et al., J. Med. Chem. 2023, 66, 5061-5078 (Year: 2023).*

* cited by examiner

*Primary Examiner* — Kortney L. Klinkel
*Assistant Examiner* — Alison Azar Salamatian

(57) ABSTRACT

The present invention discloses a pleuromutilin derivative containing thiazole-pyridine benzyl quaternary ammonium salt side chain and a preparation method and use thereof and belongs to the field of medicinal chemistry. A pleuromutilin derivative with thiazole-pyridine benzyl quaternary ammonium salt side chain is successfully prepared by structural reconstruction of pleuromutilin and then structural modification with a quaternary ammonium salt compound. This compound synthesis method has the advantages of easily available raw materials, simple operation and high product yield, and is suitable for industrial production. The results of in vitro pharmacological experiments show that the pleuromutilin derivative of the present invention have good antibacterial and anti-mycoplasma activities, as well as good solubility, and these results show that the pleuromutilin derivative is of great value in the development of an antipathogenic microorganism drug.

6 Claims, 19 Drawing Sheets

PLEUROMUTILIN DERIVATIVE CONTAINING THIAZOLE-PYRIDINE BENZYL QUATERNARY AMMONIUM SALT SIDE CHAIN AND PREPARATION METHOD AND USE THEREOF

This application claims priority to Chinese Patent Application No. CN 202210320742.7, filed on Mar. 29, 2022, which is incorporated by reference for all purposes as if fully set forth herein.

TECHNICAL FIELD

The invention belongs to the technical field of medicinal chemistry, and in particular relates to a pleuromutilin derivative containing thiazole-pyridine benzyl quaternary ammonium salt side chain and preparation method and use thereof.

BACKGROUND ART

The discovery of antibiotics has played an important role in the history of human development, but the abuse of antibiotics has led to serious drug resistance in many bacteria, posing a growing threat to human health. Existing antibiotics such as cephalosporins, aminoglycosides, macrolides and even polymyxin have been unable to treat the infections caused by some "superbugs" or are not widely available due to serious adverse reactions. The urgent task of returning to the "antibiotic era" is to solve the problem of bacterial resistance. Therefore, people continue to explore antibiotics with new antibacterial mechanisms, good bioavailability and low toxicity.

Mycoplasmas are a kind of minimal prokaryotic cell-type microorganisms which don't have cell walls, have high pleomorphism, are able to pass through bacteria filters, can be cultured and proliferated in artificial medium, and have a size of 0.1-0.3 microns. Because they can form filamentous and branched shapes, they is called mycoplasma. Mycoplasmas widely exist in humans and animals, and most of them are not pathogenic. Mycoplasmas which are pathogenic to humans mainly include *Mycoplasma pneumoniae*, Ureaplasma urealyticum, *Mycoplasma hominis*, and *Mycoplasma genitalium*. Mycoplasmas have weak pathogenicity and generally do not invade the blood, but they can bind to host cells through adhesion, obtain lipids and cholesterol from the cell membrane, and damage the cell membrane. Ureaplasma urealyticum can decompose urea and release a large amount of ammonia, which is toxic to cells.

Pleuromutilin is a broad-spectrum diterpene antibiotic with good antibacterial activity and anti-drug resistance produced by *Pleurotus*, which can effectively inhibit most Gram-positive bacteria, mycoplasmas and some Gram-negative bacteria. Pleuromutilin has a main backbone composed of three rings, and the most basic structure is an eight-member ring; the carbonyl group on the five-member ring and the hydroxyl group on C-11 are essential groups for activity. Because C-14 contains a free hydroxyl group and has no activity, most of the research at present focuses on chemical modification of the hydroxyl group of C-14. Through the modification of the C-14 side chain of pleuromutilin, two veterinary drugs and two human drugs have been successfully developed, fully realizing the leap from veterinary use to human use, showing an excellent clinical application prospect. Pleuromutilin and a derivative thereof can inhibit bacterial protein synthesis by binding to the ribosomal subunit 50S of bacteria. This unique mechanism of action and good antibacterial activity have made the research on pleuromutilin an international research hotspot.

Quaternary ammonium compound is a kind of cationic surfactant, which has the advantages of good solubility, stable chemical properties, convenient use, low toxicity and high efficiency, broad-spectrum antibacterial, etc., and is generally used in medical disinfection and sterilization and this kind of bactericide has the characteristics of strong cell penetration, good stability, low toxicity, long sterilization duration, remarkable sterilization effect etc.

SUMMARY OF THE INVENTION

In order to overcome the above-mentioned shortcomings of the prior art, the object of the present invention is to provide a pleuromutilin derivative containing thiazole-pyridine benzyl quaternary ammonium salt side chain and preparation method and use thereof, for preventing and treating infectious diseases caused by drug-resistant bacteria and mycoplasmas.

In order to achieve the above object, the present invention adopts the following technical solutions to achieve:

The invention discloses a pleuromutilin derivative containing thiazole-pyridine benzyl quaternary ammonium salt side chain, which is a compound of general formula I or a pharmaceutically acceptable salt thereof, and a solvent, an enantiomer, a diastereomer, a tautomer of the compound of general formula I or the pharmaceutically acceptable salt thereof, or their mixture in any proportion, including a racemic mixture:

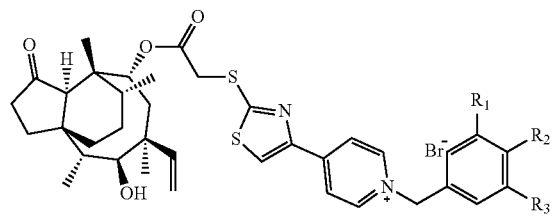

I wherein, $R_1$, $R_2$ and $R_3$ are each independently selected from hydrogen atom, methyl, trifluoromethyl, methoxy, trifluoromethoxy, tert-butyl, nitro, cyano, halogen atom or phenyl.

Preferably, the representative compound is selected from the following compounds:

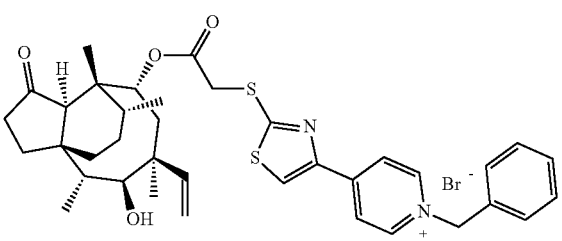

1

-continued
2
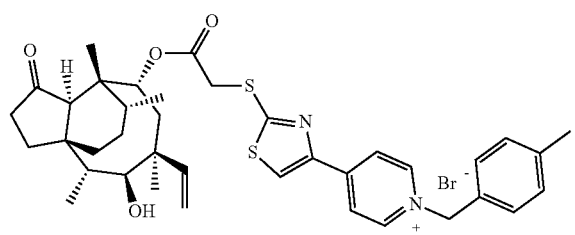
3
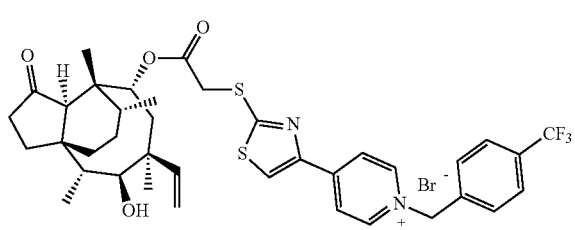
4
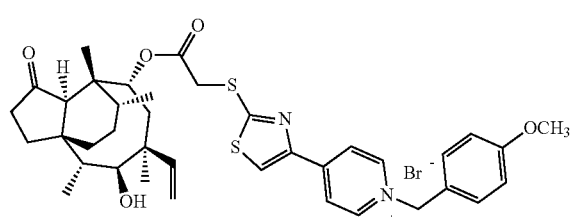
5
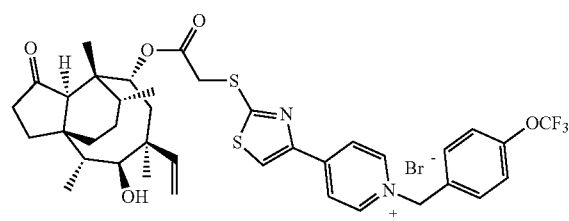
6
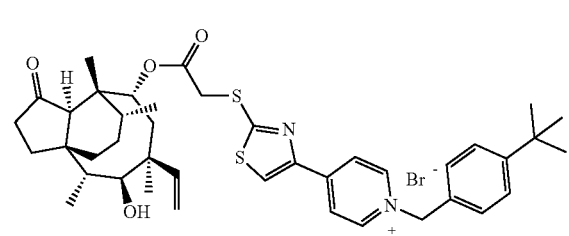
7
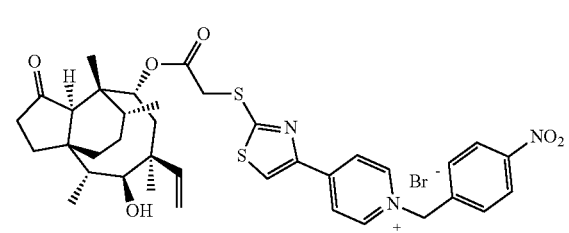
-continued
8
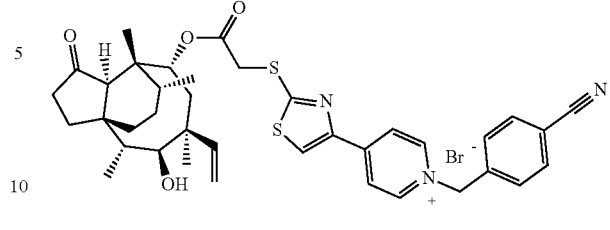
9
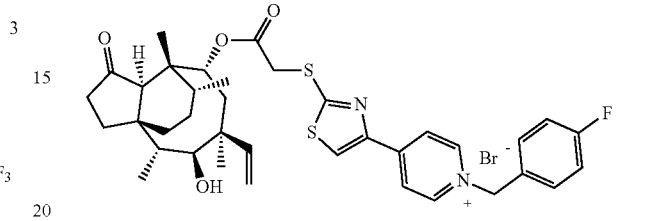
10
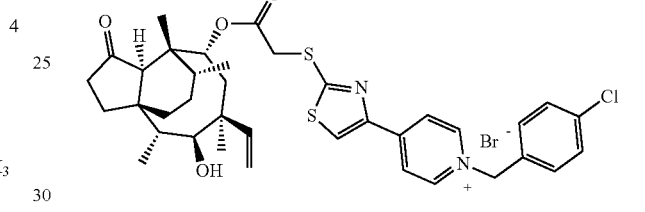
11
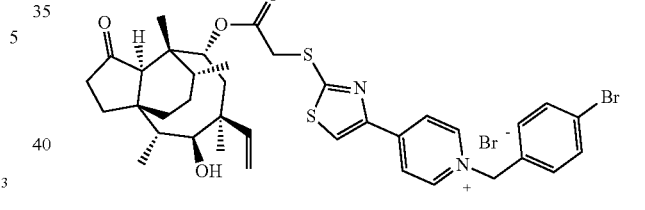
12
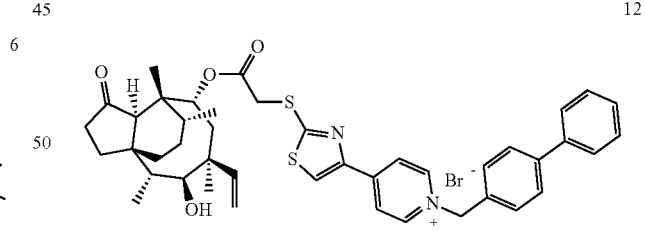
13
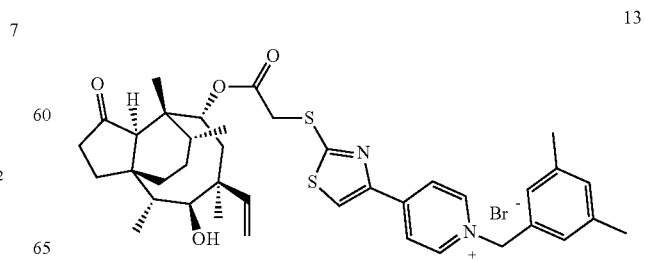

-continued

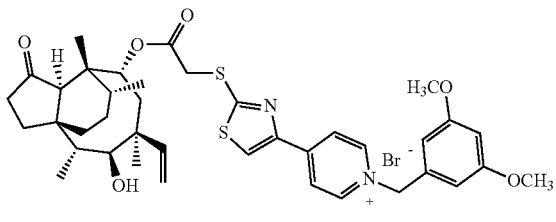

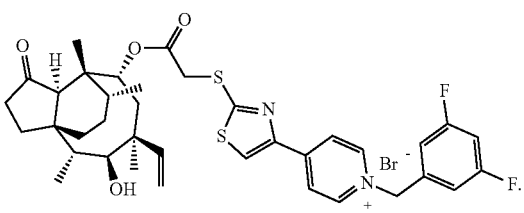

Preferably, the pharmaceutically acceptable salt is a salt formed by a compound with the structure shown in general formula I and hydrochloric acid, hydrobromic acid, sulfuric acid, nitric acid, phosphoric acid, acetic acid, fumaric acid, maleic acid, oxalic acid, malonic acid, succinic acid, citric acid, malic acid, methanesulfonic acid, ethanesulfonic acid, benzenesulfonic acid, toluenesulfonic acid, glutamic acid or aspartic acid.

The present invention also discloses a preparation method for the above-mentioned pleuromutilin derivative containing thiazole-pyridine benzyl quaternary ammonium salt side chain, comprising the following steps:

1) the pleuromutilin is reacted with p-toluenesulfonyl chloride to obtain an intermediate I;

wherein, the intermediate I is

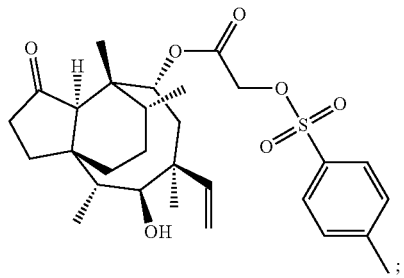 [SMILES: C=C[C@]1(C)C[C@@H](OC(=O)COS(=O)(=O)c2ccc(C)cc2)[C@]2(C)[C@H](C)CC[C@]3(CCC(=O)[C@H]32)[C@@H](C)[C@@H]1O]

2) the intermediate I prepared in step 1) and 2-mercapto-4-(4-pyridyl)thiazole are used as raw materials, dissolved in an organic solvent and reacted under catalyst catalysis and heating conditions, and an intermediate II is obtained after separation and purification;

wherein, the intermediate II is

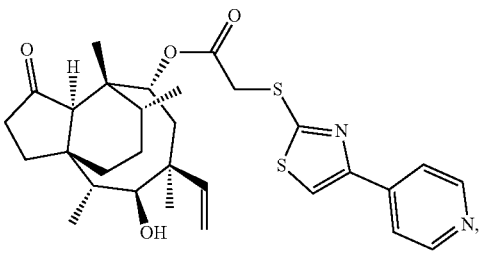 [SMILES: C=C[C@]1(C)C[C@@H](OC(=O)CSc2nc(-c3ccncc3)cs2)[C@]2(C)[C@H](C)CC[C@]3(CCC(=O)[C@H]32)[C@@H](C)[C@@H]1O]

and the catalyst is potassium carbonate and potassium iodide;

3) the intermediate II prepared in step 2) is used as a raw material, reacted with benzyl bromide compounds containing different substitutions, and after separation and purification, the pleuromutilin derivative containing thiazole-pyridine benzyl quaternary ammonium salt side chain with the structure shown in general formula I can be obtained.

Preferably, in step 1), the molar ratio of pleuromutilin to p-toluenesulfonyl chloride is 1:1.2; in step 2), the molar ratio of the intermediate I to 2-mercapto-4-(4-pyridyl)thiazole is 1:1.2; and in step 3), the molar ratio of the intermediate II to the benzyl bromide compounds with different substitutions is 1:(2-6).

Preferably, the reaction described in step 1) uses dichloromethane as a solvent, triethylamine and 4-dimethylaminopyridine as a catalyst, and is stirred and reacted at room temperature for 8 hours; the reaction described in step 2) uses N,N-dimethylformamide as a solvent, and is heated at 60° C. for 6 hours; the reaction described in step 3) uses acetonitrile, acetone or toluene as a solvent.

The present invention also discloses the use of the above-mentioned pleuromutilin derivative containing thiazole-pyridine benzyl quaternary ammonium salt side chain in the preparation of an anti-pathogenic microorganism drug.

Preferably, the anti-pathogenic microorganism drug is a pharmaceutical preparation for treating an infectious disease.

Further preferably, the infectious disease is an infectious disease of human or animal infected by mycoplasmas or drug-resistant bacteria.

Further preferably, the mycoplasmas are *Mycoplasma hyopneumoniae* standard strain J strain, *Mycoplasma hyopneumoniae* clinical isolate LH strain, *Mycoplasma hyorhina* standard strain BTS-7 strain, *Mycoplasma gallisepticum* standard strain R strain or *Mycoplasma synoviae* WVU1853 strain; the drug-resistant bacteria are multidrug-resistant *Pseudomonas aeruginosa*, multidrug-resistant *Klebsiella pneumoniae*, methicillin-resistant *Staphylococcus aureus*, vancomycin-resistant *Enterococcus faecalis* or carbapenem-resistant *Acinetobacter baumannii*.

Preferably, the pharmaceutical preparation contains one or more pharmaceutically acceptable carriers, excipients or diluents.

The present invention also discloses an antibiotic drug, the drug contains an effective amount of the above-mentioned pleuromutilin derivative containing thiazole-pyridine benzyl quaternary ammonium salt side chain, and the balance is pharmaceutical excipients or other compatible drugs.

Compared with the prior art, the present invention has the following beneficial effects:

The present invention provides a pleuromutilin derivative containing thiazole-pyridine benzyl quaternary ammonium salt side chain. A pleuromutilin derivative with thiazole-pyridine benzyl quaternary ammonium salt side chain was successfully prepared by structural reconstruction of pleuromutilin and then structural modification with a quaternary ammonium salt compound. The in vitro antibacterial activity assay shows that the compounds 1-15 synthesized by the present invention can produce inhibitory effects on different bacterial strains, and the inhibitory ability of most of the compounds to drug-resistant bacteria is stronger than that of three marketed drugs (retapamulin, tiamulin, and valnemulin). Preferred compound 2 has the best antibacterial effect, with MIC of 0.0625 µg/mL for ATCC 25923 and ATCC 29213, MIC of 1 µg/mL for ATCC 19606, and MIC of 0.0625 and 0.5 µg/mL for *Escherichia coli* (ATCC 25922 and CMCC 44103) respectively. The inhibitory effect of the preferred compound 7 on all clinical drug-resistant bacteria (MDR-PA18-993, 18-756, 18-126, MDR-KP18-893, 18-754, 18-1482, MRSA 18-171, 18-209, 18-575, VRE18-94, 18-80, 18-507, CR-AB18-184, 18-560, and 18-882) is better than that of the marketed drug ritamoline and has broad-spectrum antibacterial activity. The determination of anti-mycoplasma activity shows that the anti-mycoplasma effect of the preferred compound 7 is better than that of the marketed pleuromutilin antibiotic tiamulin. The above experiments show that this type of compound has good antibacterial activity in vitro and strong mycoplasma inhibitory activity, improves the poor solubility of pleuromutilin derivatives, can be applied to the prevention and treatment of an infection disease caused by drug-resistant bacteria and mycoplasmas, and has a very good medical development value.

The present invention provides a preparation method for the pleuromutilin derivative containing thiazole-pyridine benzyl quaternary ammonium salt side chain described above, which method has the advantages of easily available raw materials, high operation safety, mild reaction conditions, low cost and high yield of 72.51%-89.19%, and is suitable for industrial production.

DETAILED DESCRIPTION OF EMBODIMENTS

Figure 1:
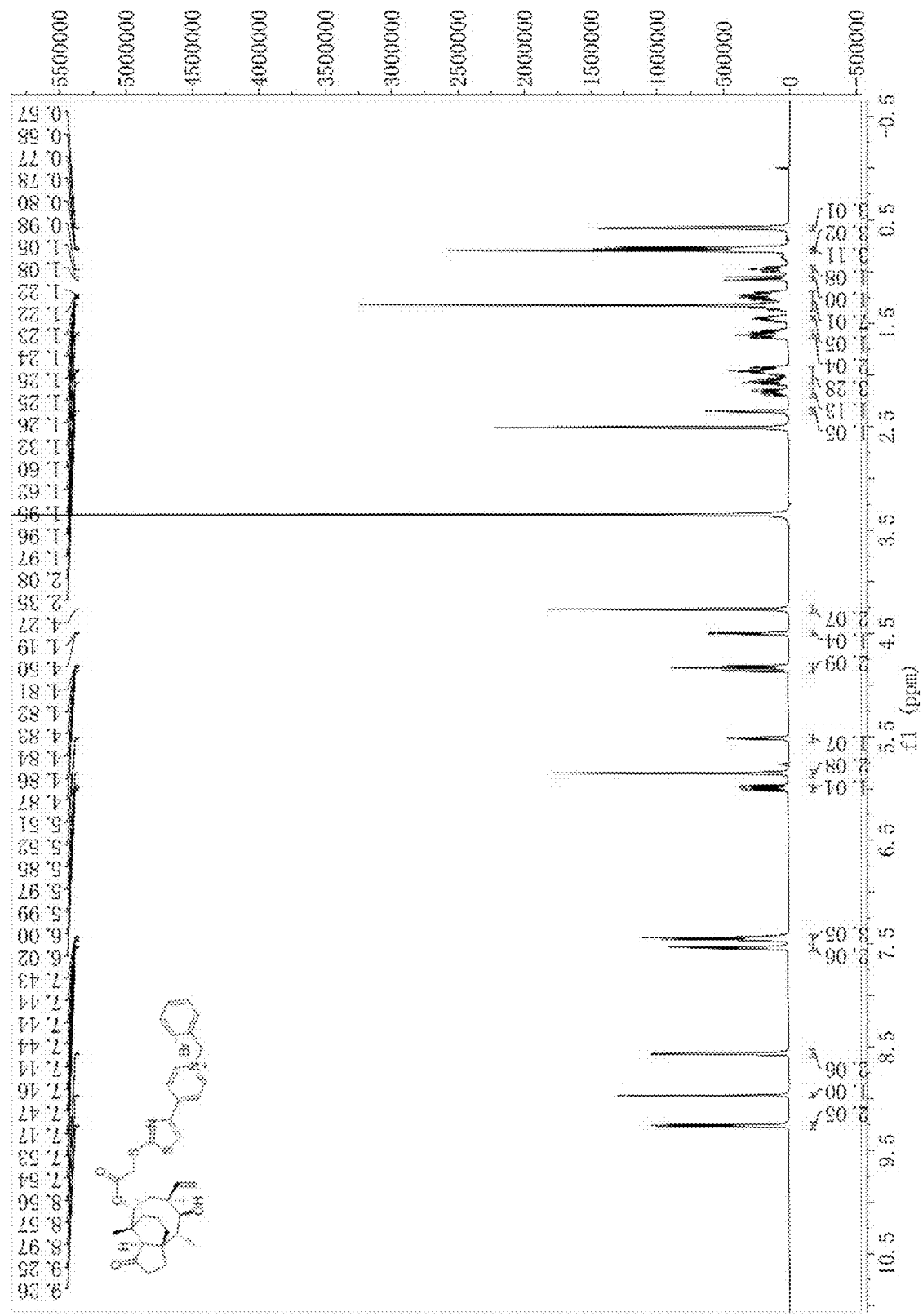
FIG. 1 is the H NMR spectrum of compound 1 of the present invention in deuterated DMSO.

In order to enable those skilled in the art to better understand the solutions of the present invention, the technical solutions in the embodiment of the invention will be described clearly and completely with the attached drawings in the embodiment of the invention. Obviously, the described embodiment is only a part of the embodiments of the invention, but not all the embodiments. Based on the embodiments of the present invention, all other embodiments that would have been obtained by those of ordinary skill in the art without involving any inventive effort shall fall within the scope of protection of the present invention.

It should be noted that the terms "first" and "second" in the description and claims of the present invention and the above drawings are used to distinguish similar objects, but not necessarily used to describe a particular order or sequence. It should be understood that the data thus used are interchangeable under appropriate circumstances such that the embodiments of the invention described herein can be practiced in a sequence other than those illustrated or described herein. Furthermore, the terms "comprise" and "have", as well as any variations thereof, are intended to encompass a non-exclusive inclusion, for example, a process, method, system, product or device comprising a series of steps or units is not necessarily limited to those explicitly listed, but may include other steps or units not explicitly listed or inherent to the process, method, product or device.

The present invention is described in further detail below in conjunction with accompanying drawings:

The present invention provides a pleuromutilin derivative containing thiazole-pyridine benzyl quaternary ammonium salt side chain, which is a compound of general formula I or a pharmaceutically acceptable salt thereof, and a solvent, an enantiomer, a diastereomer, a tautomer of the compound of general formula I or the pharmaceutically acceptable salt thereof, or their mixture in any proportion, including a racemic mixture:

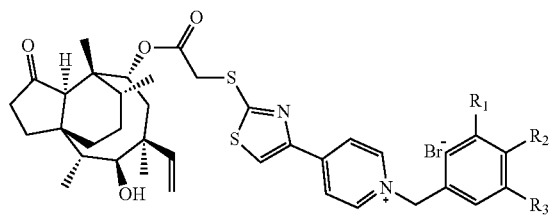

wherein, $R_1$, $R_2$ and $R_3$ are each independently selected from hydrogen atom, methyl, trifluoromethyl, methoxy, trifluoromethoxy, tert-butyl, nitro, cyano, halogen atom or phenyl; the term "halogen" refers to fluoro, chloro, bromo and iodo; the pharmaceutically acceptable salt is a salt formed by a compound with the structure shown in general formula I and hydrochloric acid, hydrobromic acid, sulfuric acid, nitric acid, phosphoric acid, acetic acid, fumaric acid, maleic acid, oxalic acid, malonic acid, succinic acid, citric acid, malic acid, methanesulfonic acid, ethanesulfonic acid, benzenesulfonic acid, toluenesulfonic acid, glutamic acid or aspartic acid.

The present invention provides a preparation method for the pleuromutilin derivative containing thiazole-pyridine benzyl quaternary ammonium salt side chain described above, the method comprises the following steps: (1) the pleuromutilin is reacted with p-toluenesulfonyl chloride to obtain an intermediate I, and the reaction formula is as follows:

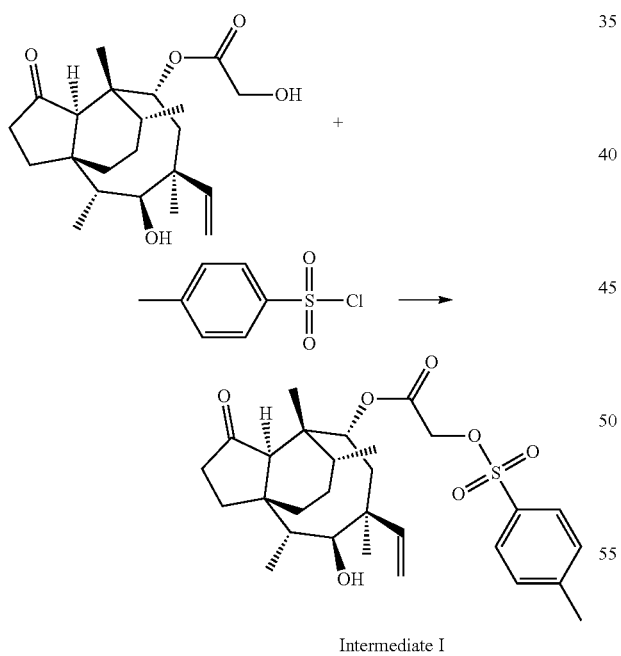

Intermediate I wherein, the reaction uses dichloromethane as a solvent, triethylamine and 4-dimethylaminopyridine as catalysts, and the reaction is stirred at room temperature for 8 hours; the molar ratio of pleuromutilin to p-toluenesulfonyl chloride is 1:1.2;

(2) the intermediate I prepared in step (1) and 2-mercapto-4-(4-pyridyl)thiazole are used as raw materials, dissolved in an organic solvent and reacted under catalyst catalysis and heating conditions, and an intermediate II is obtained after separation and purification, and the reaction formula is as follows:

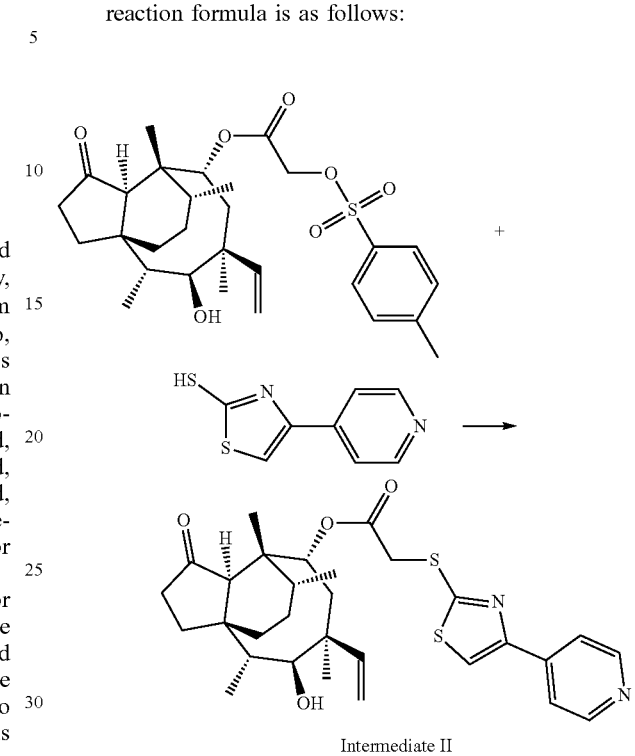

Intermediate II wherein, the reaction uses N,N-dimethylformamide as a solvent and the reaction is heated at 60° C. for 6 hours; the molar ratio of intermediate I to 2-mercapto-4-(4-pyridyl)thiazole is 1:1.2; the catalyst is potassium carbonate and potassium iodide; the specific operation of the purification is preferably that: after the reaction is completed, the reaction mixture is diluted with saturated ammonium chloride aqueous solution, extracted with ethyl acetate, and the ethyl acetate phase was collected, and separated and purified by column chromatography to obtain the intermediate II;

(3) the intermediate II prepared in step (2) is used as a raw material, reacted with benzyl bromide compounds containing different substitutions, and after separation and purification, the pleuromutilin derivative containing thiazole-pyridine benzyl quaternary ammonium salt side chain with the structure shown in general formula I can be obtained, and the reaction formula is as follows:

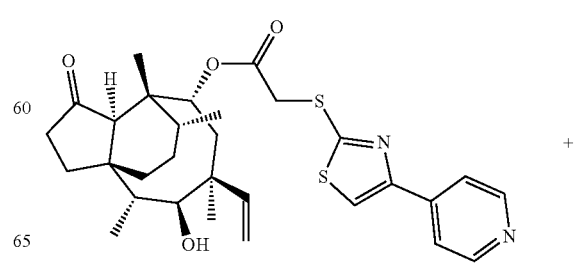

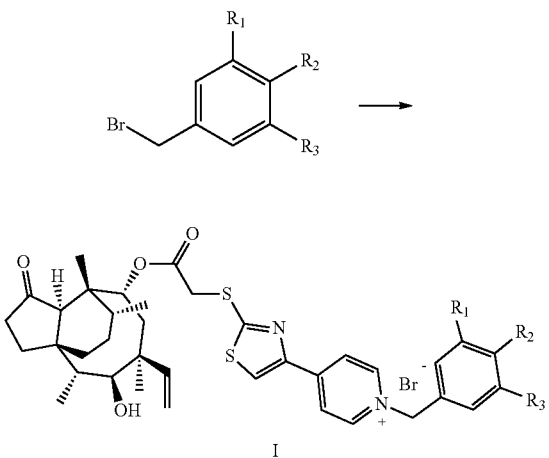

wherein, the reaction uses acetonitrile, acetone, toluene as solvents, more preferably acetonitrile; in the reaction, the molar ratio of the intermediate II to the benzyl bromide compounds containing different substitutions is 1:(2-6), further optimized to 1:4. The specific operation of the purification is preferably that: after the reaction is completed, the reaction mixture is concentrated under reduced pressure to remove the solvent, then separated and purified by column chromatography to obtain the product of interest, and the ratio of the eluents is dichloromethane:methanol=10:1.

1. SPECIFIC EXAMPLES OF SYNTHESIZING COMPOUNDS 1-15

The structural formula of the representative compound of the present invention is shown below:

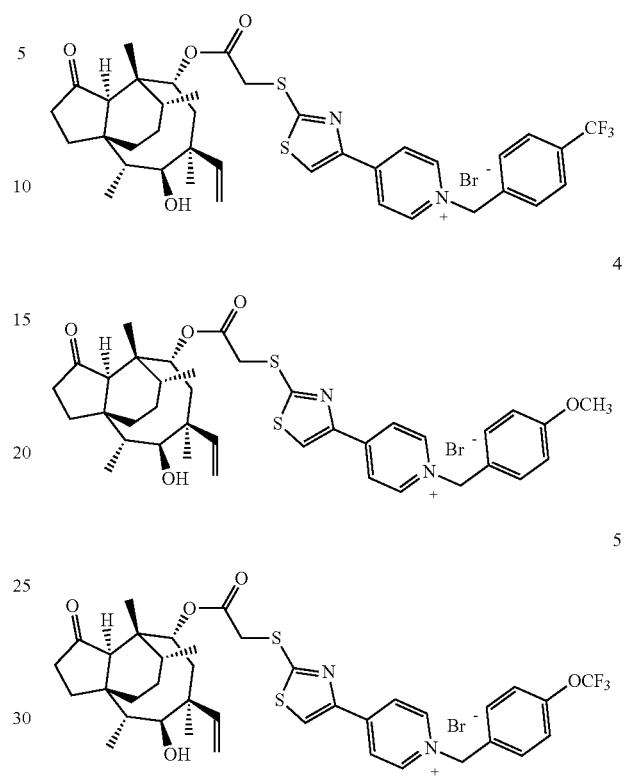

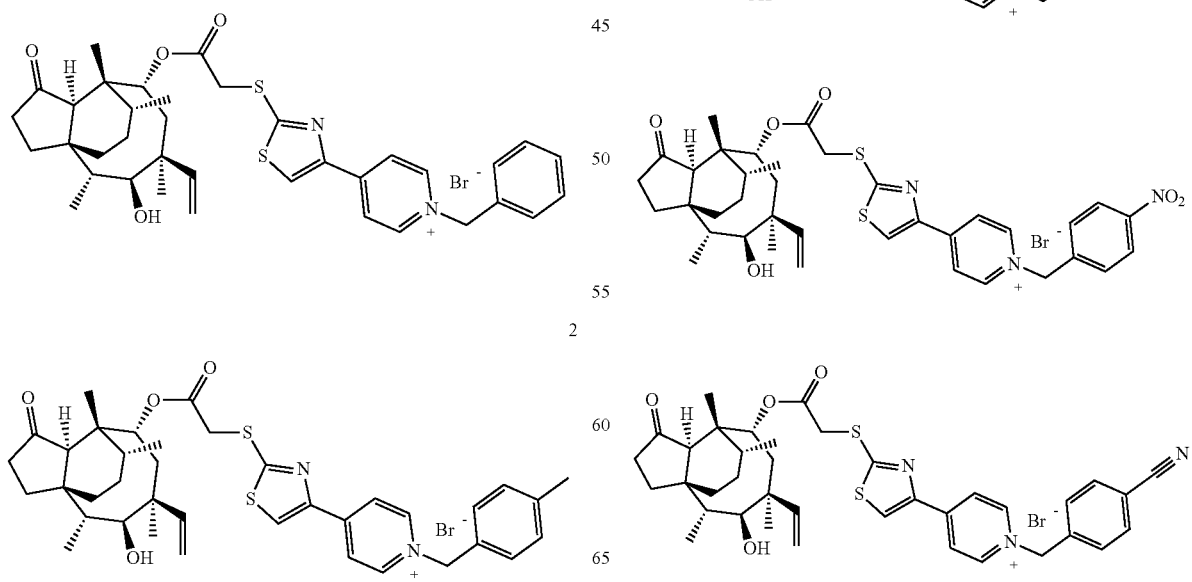

-continued

9

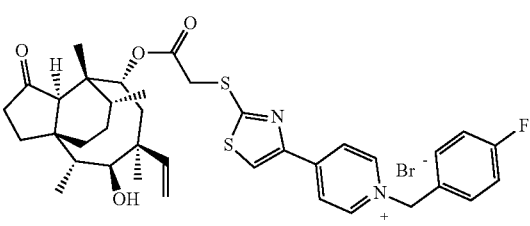

10

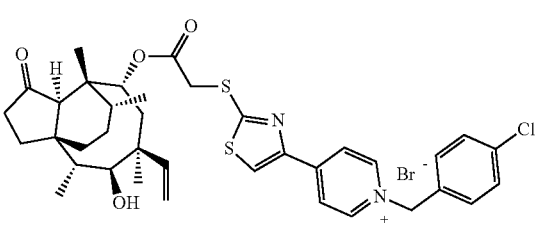

11

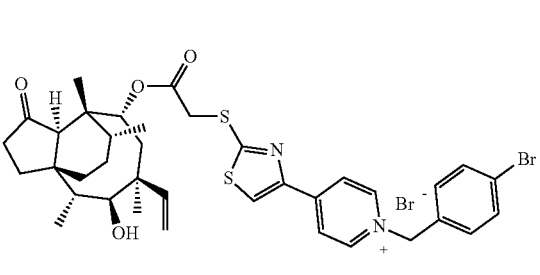

12

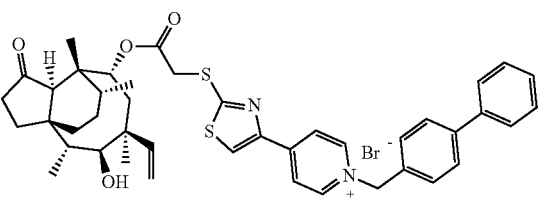

13

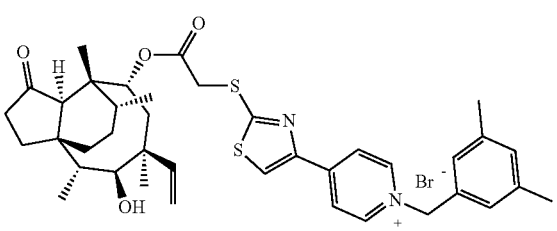

14

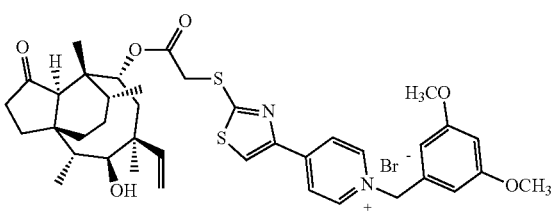

-continued

15

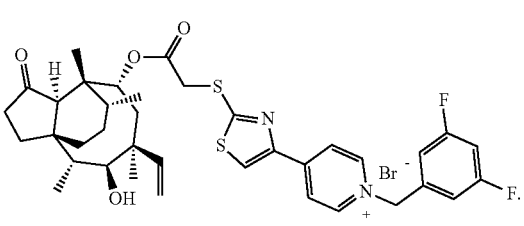

The synthesis examples of the above compounds are given below. The structures of the compounds are characterized by NMR.

Example 1

(1) Preparation of Intermediate I

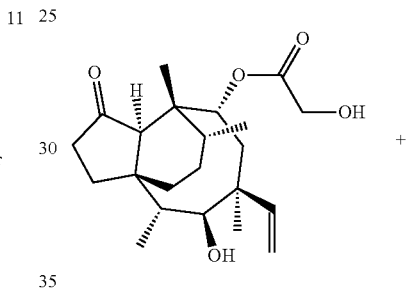

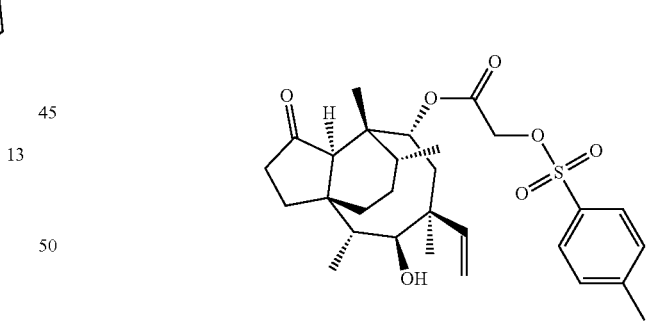

9.5 g (25 mmol) pleuromutilin and 5.7 g (30 mmol) p-toluenesulfonyl chloride were placed in a reactor, dissolved in 150 mL of dichloromethane, and 10.5 mL (75 mmol) of triethylamine and 305.4 mg (2.5 mmol) of 4-dimethylaminopyridine was added and stirred at room temperature for 8 hours, and TLC was used for monitoring. After the reaction, the reaction liquid was concentrated under reduced pressure to remove the solvent, and the obtained solid was washed with saturated aqueous sodium bicarbonate (100 mL) and water (100 mL), and dried to obtain 12.7 g of the intermediate I with a yield of 95.32%.

(2) Preparation of Intermediate II

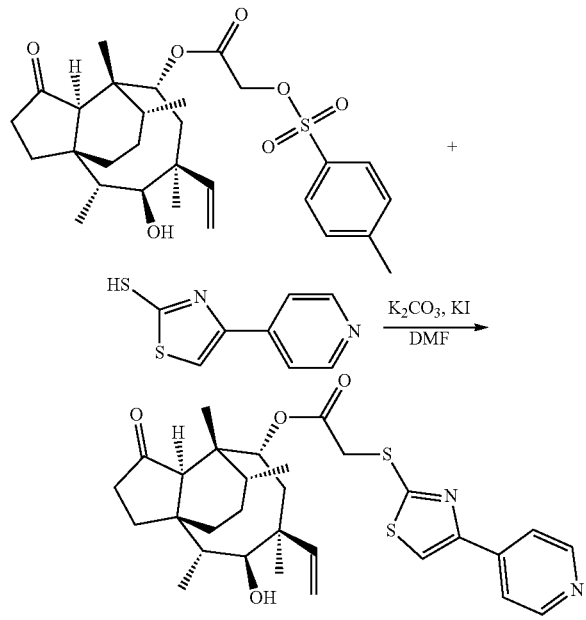

10.7 g (20 mmol) of the intermediate I and 4.7 g (24 mmol) of 2-mercapto-4-(4-pyridyl)thiazole were placed in a reactor and dissolved in 100 mL of N,N-dimethylformamide, 5.5 g (40 mmol) of potassium carbonate and 332 mg (2 mmol) of potassium iodide were added thereto, and the reaction was heated at 60° C. for 6 hours, and TLC was used for monitoring. After the reaction, the reaction liquid was diluted with a saturated aqueous ammonium chloride solution, extracted with ethyl acetate, and the ethyl acetate phase was collected, separated and purified by column chromatography (200-300 mesh silica gel powder was used as the stationary phase, dichloromethane:methanol (V:V)=20:1 as the mobile phase), and dried to obtain 10.2 g of the intermediate II with a yield of 91.93%.

(3) Synthesis of Compound 1

Compound 1: Preparation of 1-Benzyl-4-(2-(((8-hydroxy-4,7,9,12-tetramethyl-3-oxy-7-vinyldecahydro-4,9a-propanecyclopenta[8]cyclen-5-yl)oxy)-2-oxoethyl)thiothiazol-4-yl)pyridyl bromide salt

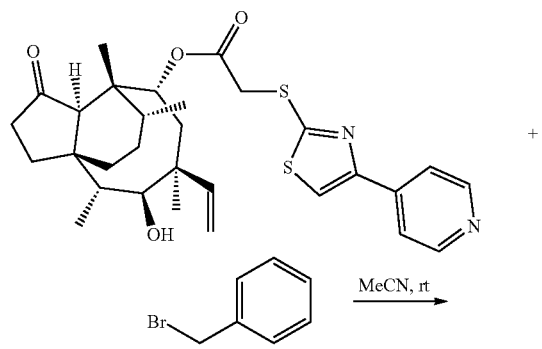

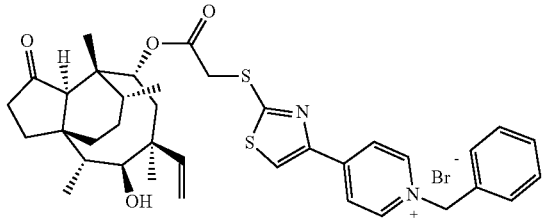

Figure 2:
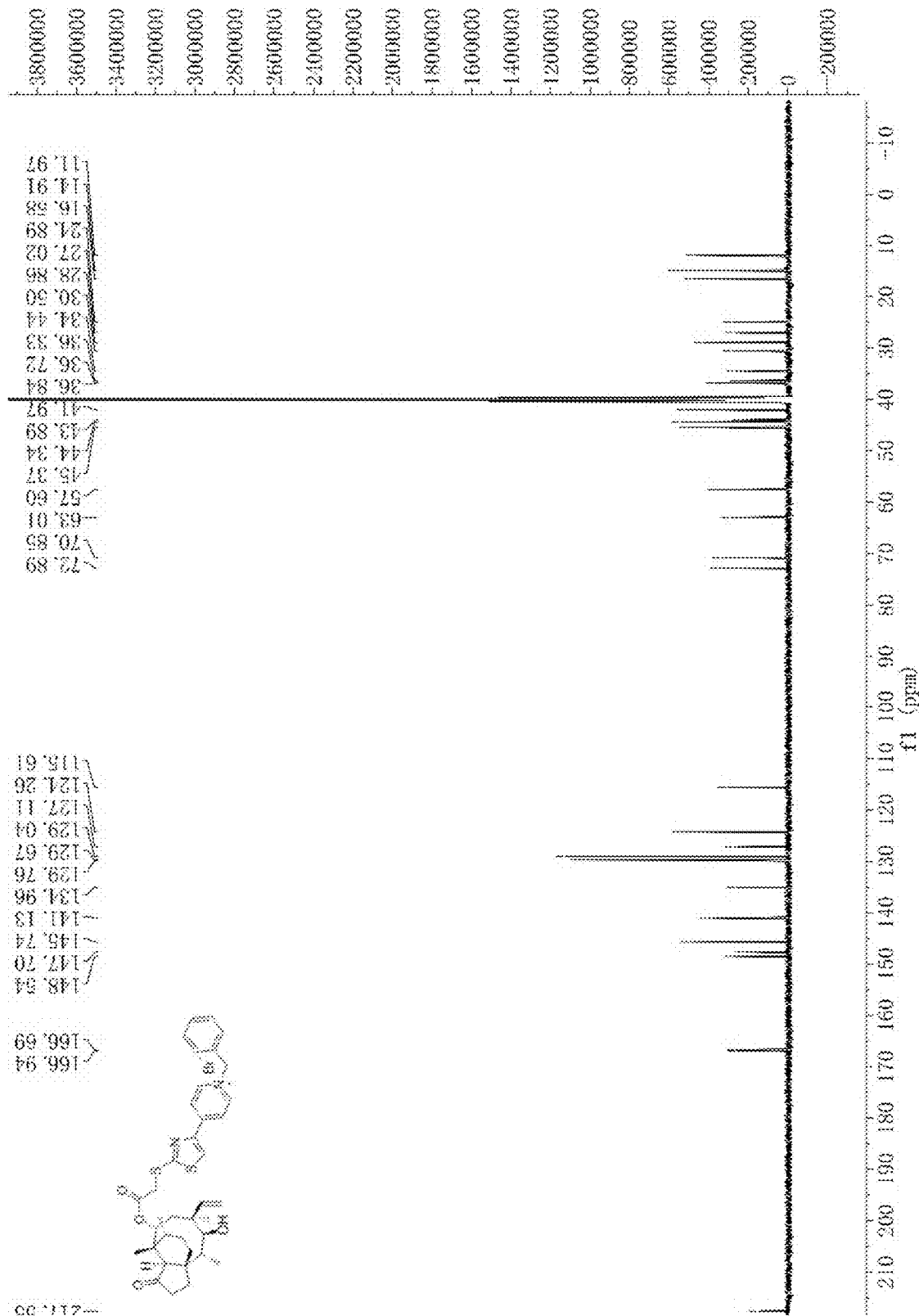
FIG. 2 is the C NMR spectrum of compound 1 in deuterated DMSO in the present invention.

166.4 mg (0.3 mmol) of the intermediate II synthesized in step (2) and 205.2 mg (1.2 mmol) of benzyl bromide were placed in a reactor, dissolved in 5 mL of acetonitrile, stirred overnight at room temperature, and monitored by TLC. After the reaction, the reaction mixture was concentrated under reduced pressure to remove acetonitrile, separated and purified by column chromatography (dichloromethane: methanol (V:V)=10:1), and dried to obtain 193.5 mg of compound 1 with a yield of 88.85%. The H NMR spectrum of compound 1 in deuterated DMSO is shown in FIG. 1, and the C NMR spectrum in deuterated DMSO is shown in FIG. 2.

$^1$H NMR (600 MHz, DMSO) δ 9.26 (d, J=6.5 Hz, 2H), 8.97 (s, 1H), 8.56 (d, J=6.5 Hz, 2H), 7.54 (d, J=7.6 Hz, 2H), 7.49-7.40 (m, 3H), 5.99 (dd, J=17.8, 11.2 Hz, 1H), 5.85 (s, 2H), 5.51 (d, J=8.4 Hz, 1H), 4.91-4.78 (m, 2H), 4.50 (d, J=6.0 Hz, 1H), 4.27 (s, 2H), 2.35 (s, 1H), 2.17 (dd, J=19.2, 10.9 Hz, 1H), 2.11-1.91 (m, 3H), 1.68-1.56 (m, 2H), 1.50-1.42 (m, 1H), 1.38-1.19 (m, 7H), 1.06 (d, J=15.8 Hz, 1H), 1.02-0.93 (m, 1H), 0.80 (s, 3H), 0.77 (d, J=7.0 Hz, 3H), 0.58 (d, J=7.0 Hz, 3H).

$^{13}$C NMR (151 MHz, DMSO) δ 217.55, 166.94, 166.69, 148.54, 147.70, 145.74, 141.13, 134.96, 129.76, 129.67, 129.04, 127.11, 124.26, 115.61, 72.89, 70.85, 63.01, 57.60, 45.37, 44.34, 43.89, 41.97, 36.84, 36.72, 36.33, 34.44, 30.50, 28.86, 27.02, 24.89, 16.58, 14.91, 11.97.

Example 2

Compound 2: Preparation of 1-(4-Methylbenzyl)-4-(2-((2-((8-hydroxy-4,7,9,12-tetramethyl-3-oxo-7-vinyldecahydro-4,9a-propancyclopent[8]cyclen-5-yl)oxy)-2-oxoethyl)thio)thiazol-4-yl)pyridyl bromide salt

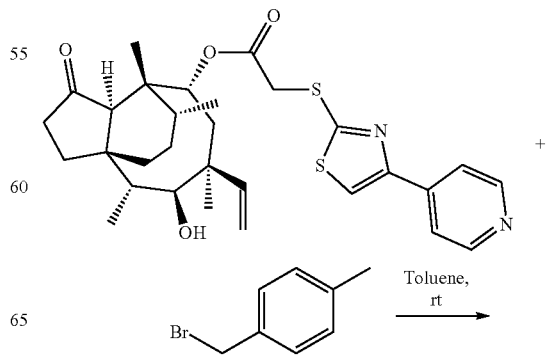

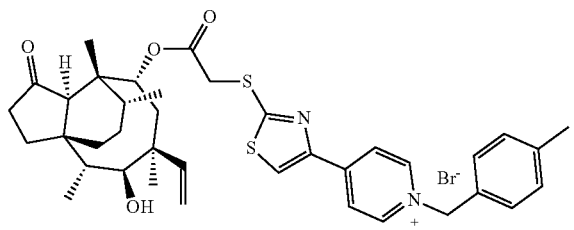
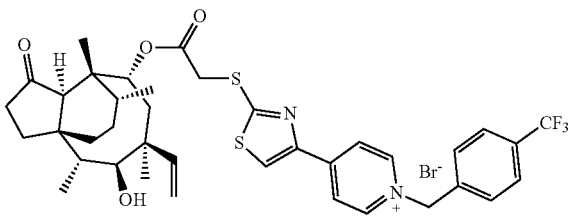

Figure 3:
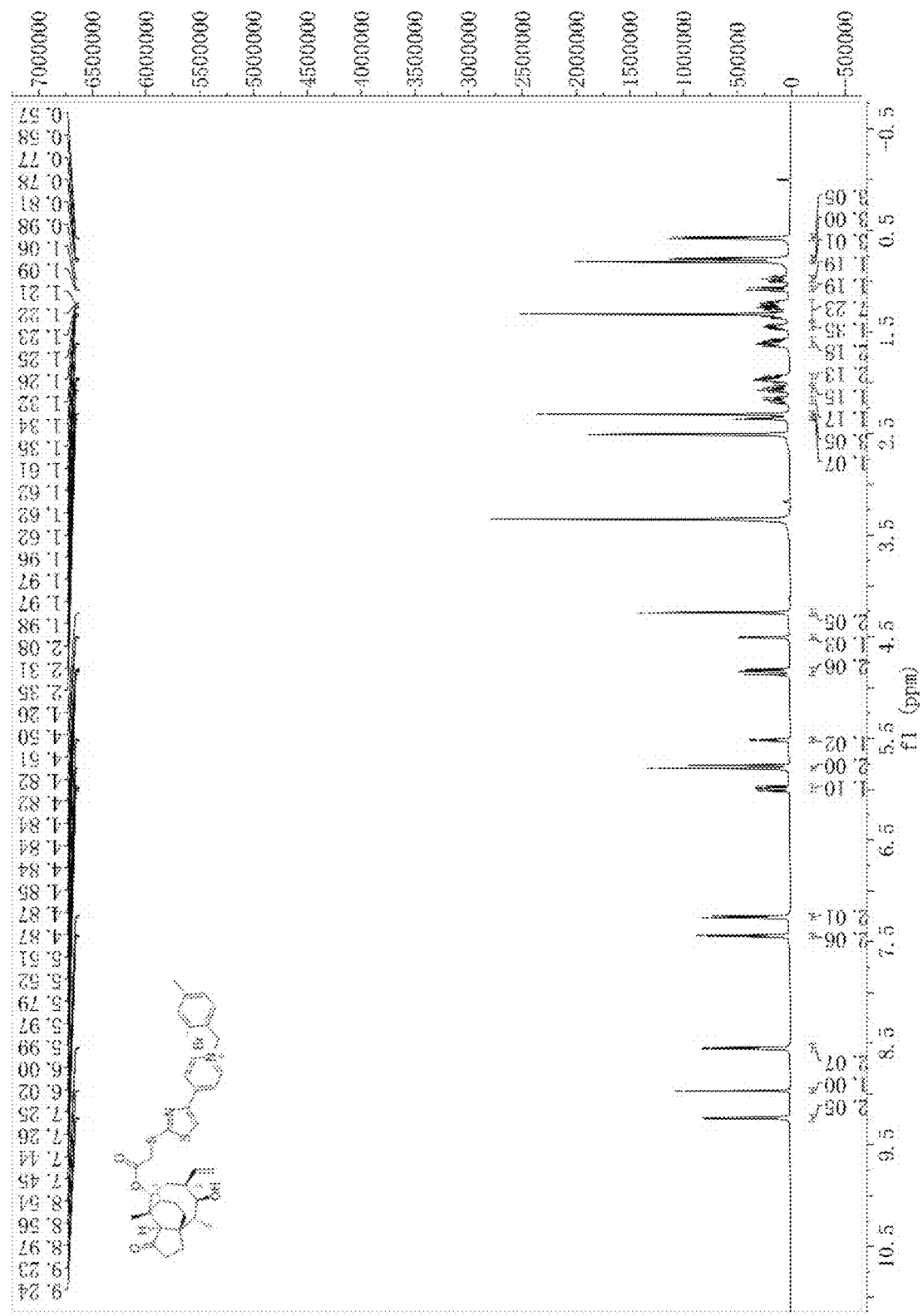
FIG. 3 is the H NMR spectrum of compound 2 in deuterated DMSO in the present invention.
Figure 4:
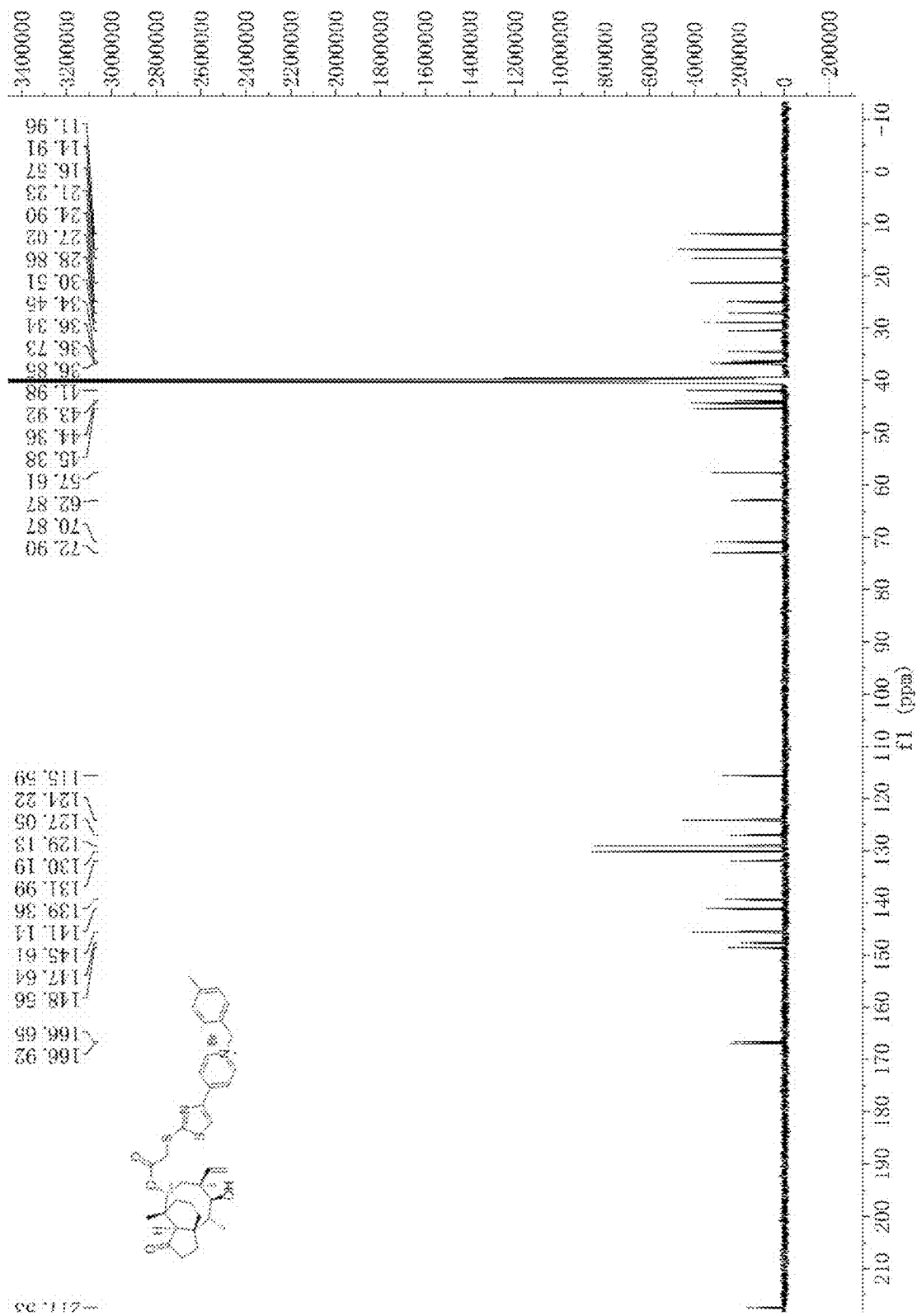
FIG. 4 is the C NMR spectrum of compound 2 in deuterated DMSO in the present invention.

The preparation method of intermediate I and intermediate II is the same as in Example 1. 166.4 mg (0.3 mmol) of intermediate II and 222.1 mg (1.2 mmol) of p-methylbenzyl bromide were placed in a reactor, dissolved in 5 mL of toluene, stirred overnight at room temperature, and monitored by TLC. After the reaction, the reaction mixture was concentrated under reduced pressure to remove toluene, separated and purified by column chromatography (dichloromethane:methanol (V:V)=10:1), and dried to obtain 183.7 mg of compound 2 with a yield of 82.79%. The H NMR spectrum of compound 2 in deuterated DMSO is shown in FIG. 3, and the C NMR spectrum in deuterated DMSO is shown in FIG. 4.

$^1$H NMR (600 MHz, DMSO) δ 9.24 (d, J=6.5 Hz, 2H), 8.97 (s, 1H), 8.55 (d, J=6.5 Hz, 2H), 7.44 (d, J=7.9 Hz, 2H), 7.26 (d, J=7.8 Hz, 2H), 5.99 (dd, J=17.8, 11.2 Hz, 1H), 5.79 (s, 2H), 5.51 (d, J=8.4 Hz, 1H), 4.90-4.79 (m, 2H), 4.51 (d, J=6.1 Hz, 1H), 4.26 (s, 2H), 2.35 (s, 1H), 2.31 (s, 3H), 2.17 (dd, J=19.3, 11.0 Hz, 1H), 2.11-2.01 (m, 1H), 2.01-1.91 (m, 2H), 1.66-1.55 (m, 2H), 1.50-1.42 (m, 1H), 1.38-1.19 (m, 7H), 1.07 (d, J=15.8 Hz, 1H), 1.02-0.93 (m, 1H), 0.81 (s, 3H), 0.78 (d, J=7.0 Hz, 3H), 0.57 (d, J=7.1 Hz, 3H).

$^{13}$C NMR (151 MHz, DMSO) δ 217.53, 166.92, 166.65, 148.56, 147.64, 145.61, 141.14, 139.36, 131.99, 130.19, 129.13, 127.05, 124.22, 115.59, 72.90, 70.87, 62.87, 57.61, 45.38, 44.36, 43.92, 41.98, 36.85, 36.73, 36.34, 34.45, 30.51, 28.86, 27.02, 24.90, 21.23, 16.57, 14.91, 11.96.

Figure 5:
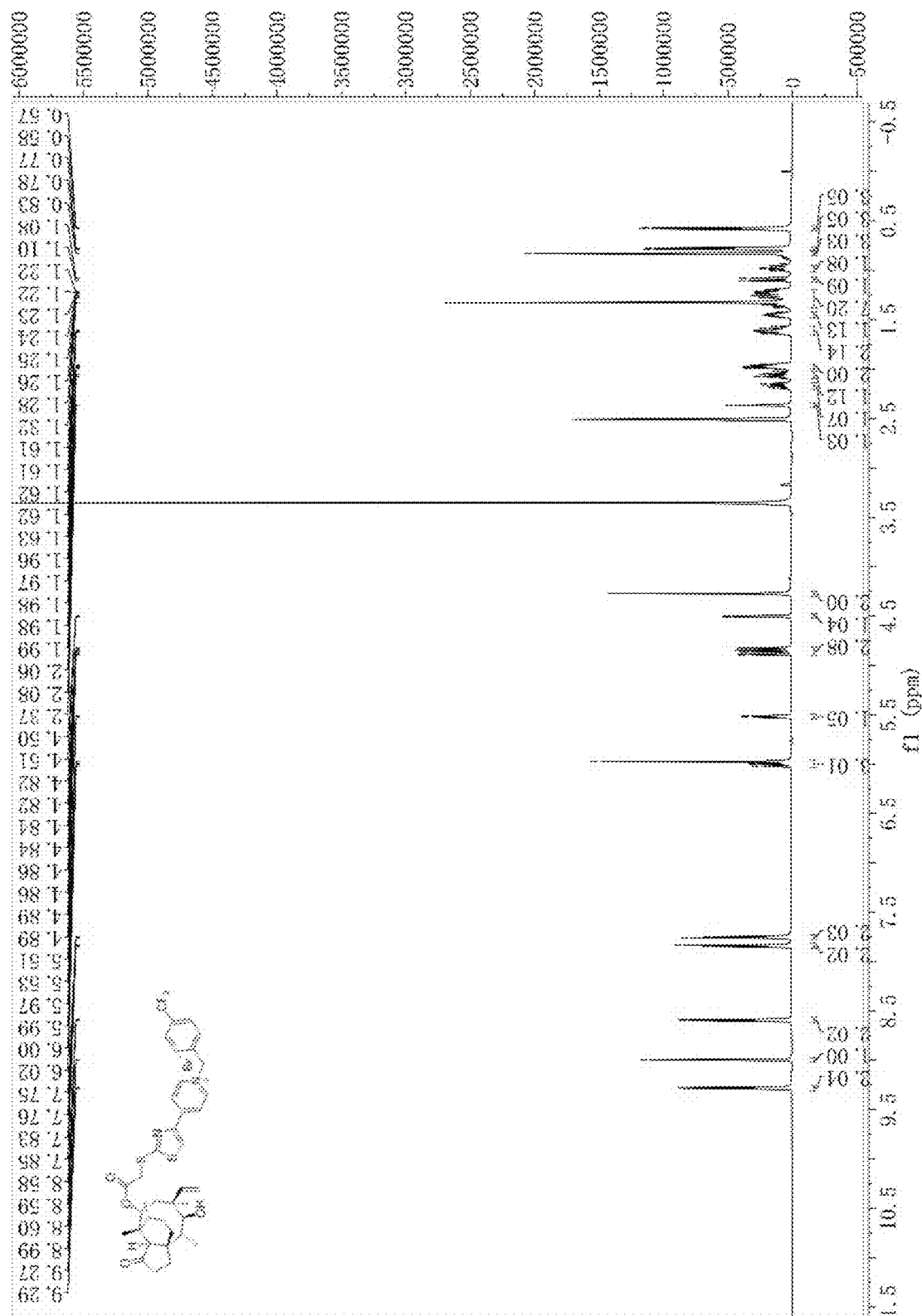
FIG. 5 is the H NMR spectrum of compound 3 in deuterated DMSO in the present invention.
Figure 6:
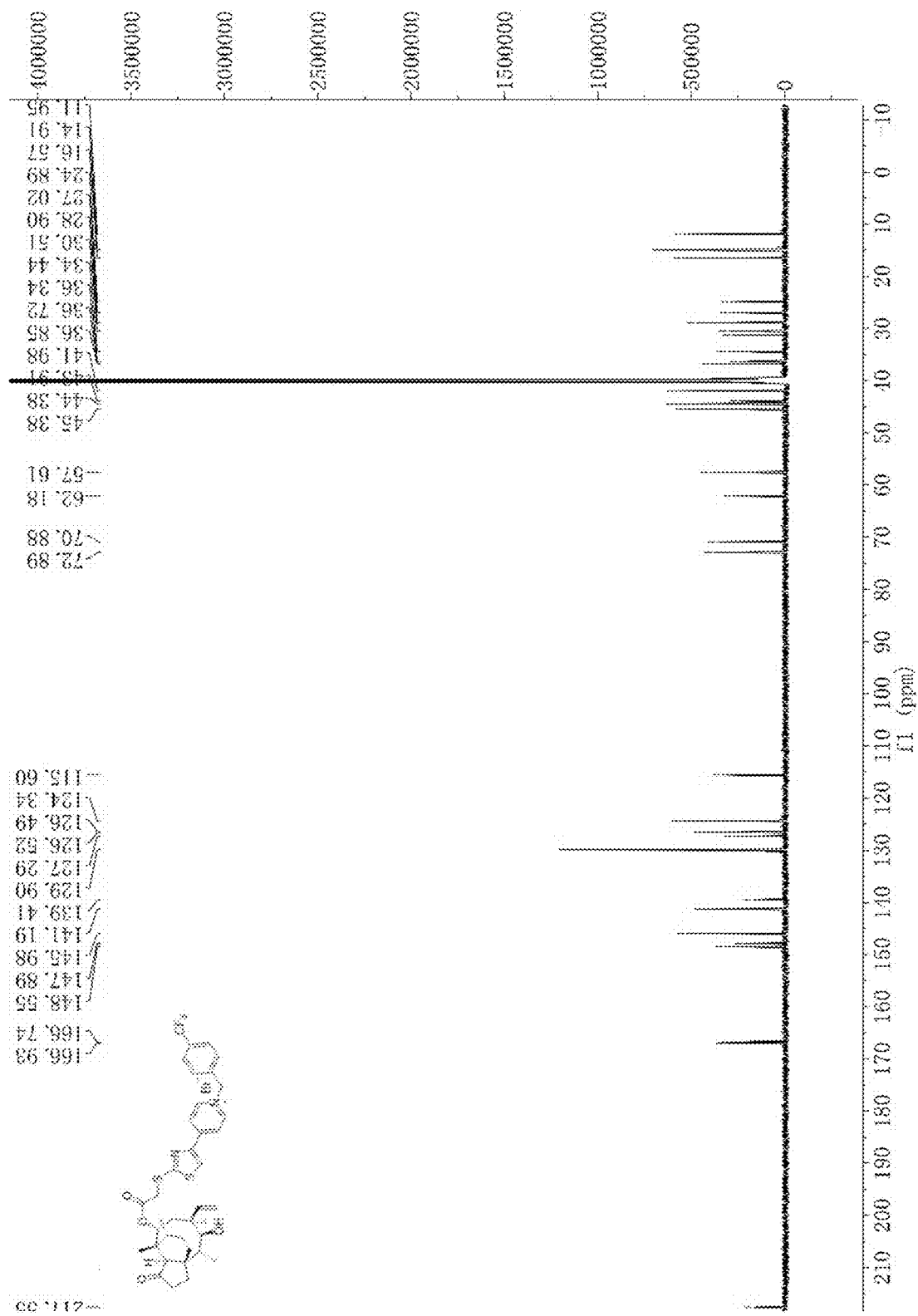
FIG. 6 is the C NMR spectrum of compound 3 in deuterated DMSO in the present invention.

The preparation method of intermediate I and intermediate II is the same as in Example 1. 166.4 mg (0.3 mmol) of intermediate II and 286.8 mg (1.2 mmol) of p-trifluoromethylbenzyl bromide were placed in a reactor, dissolved in 5 mL of acetone, stirred overnight at room temperature, and monitored by TLC. After the reaction, the reaction mixture was concentrated under reduced pressure to remove acetone, separated and purified by column chromatography (dichloromethane:methanol (V:V)=10:1), and dried to obtain 186.8 mg of compound 3 with a yield of 78.43%. The H NMR spectrum of compound 3 in deuterated DMSO is shown in FIG. 5, and the C NMR spectrum in deuterated DMSO is shown in FIG. 6.

$^1$H NMR (600 MHz, DMSO) δ 9.28 (d, J=6.5 Hz, 2H), 8.99 (s, 1H), 8.61-8.57 (m, 2H), 7.84 (d, J=8.1 Hz, 2H), 7.75 (d, J=8.0 Hz, 2H), 6.15-5.87 (m, 3H), 5.52 (d, J=8.3 Hz, 1H), 4.91-4.81 (m, 2H), 4.51 (d, J=6.0 Hz, 1H), 4.27 (s, 2H), 2.37 (s, 1H), 2.17 (dd, J=19.2, 10.9 Hz, 1H), 2.11-2.01 (m, 1H), 2.02-1.94 (m, 2H), 1.66-1.56 (m, 2H), 1.50-1.41 (m, 1H), 1.39-1.17 (m, 7H), 1.09 (d, J=15.8 Hz, 1H), 1.02-0.92 (m, 1H), 0.83 (s, 3H), 0.78 (d, J=7.0 Hz, 3H), 0.58 (d, J=7.1 Hz, 3H).

$^{13}$C NMR (151 MHz, DMSO) δ 217.55, 166.93, 166.74, 148.55, 147.89, 145.98, 141.19, 139.41, 129.90, 127.29, 126.52, 126.49, 124.34, 115.60, 72.89, 70.88, 62.18, 57.61, 45.38, 44.38, 43.91, 41.98, 36.85, 36.72, 36.34, 34.44, 31.38, 28.90, 27.02, 24.89, 16.57, 14.91, 11.95.

Example 3

Compound 3: Preparation of 1-(4-(trifluoromethyl)benzyl)-4-(2-(8-hydroxy-4,7,9,12-tetramethyl-3-oxo-7-vinyldecahydro-4,9a-propancyclopent[8]cyclen-5-yl)oxy)-2-oxoethyl)thiazol-4-yl)pyridyl bromide salt Example 4

Compound 4: Preparation of 1-(4-(methoxy)benzyl)-4-(2-(8-hydroxy-4,7,9,12-tetramethyl-3-oxo-7-vinyldecahydro-4,9a-propancyclopent[8]cyclen-5-yl)oxy)-2-oxoethyl)thiazol-4-yl)pyridyl bromide salt

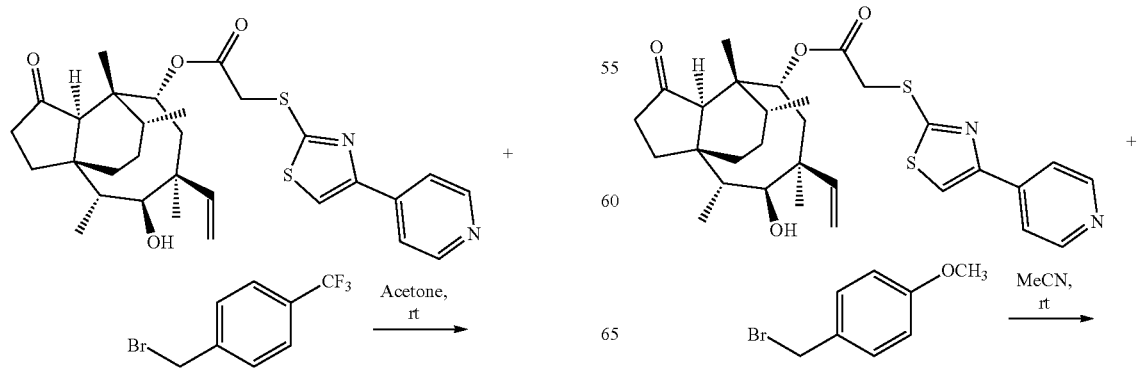

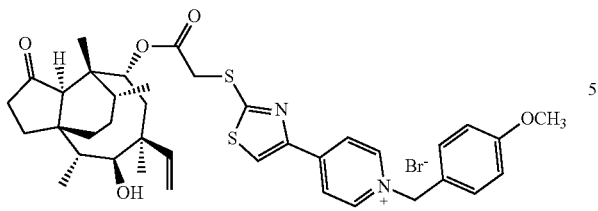

Figure 7:
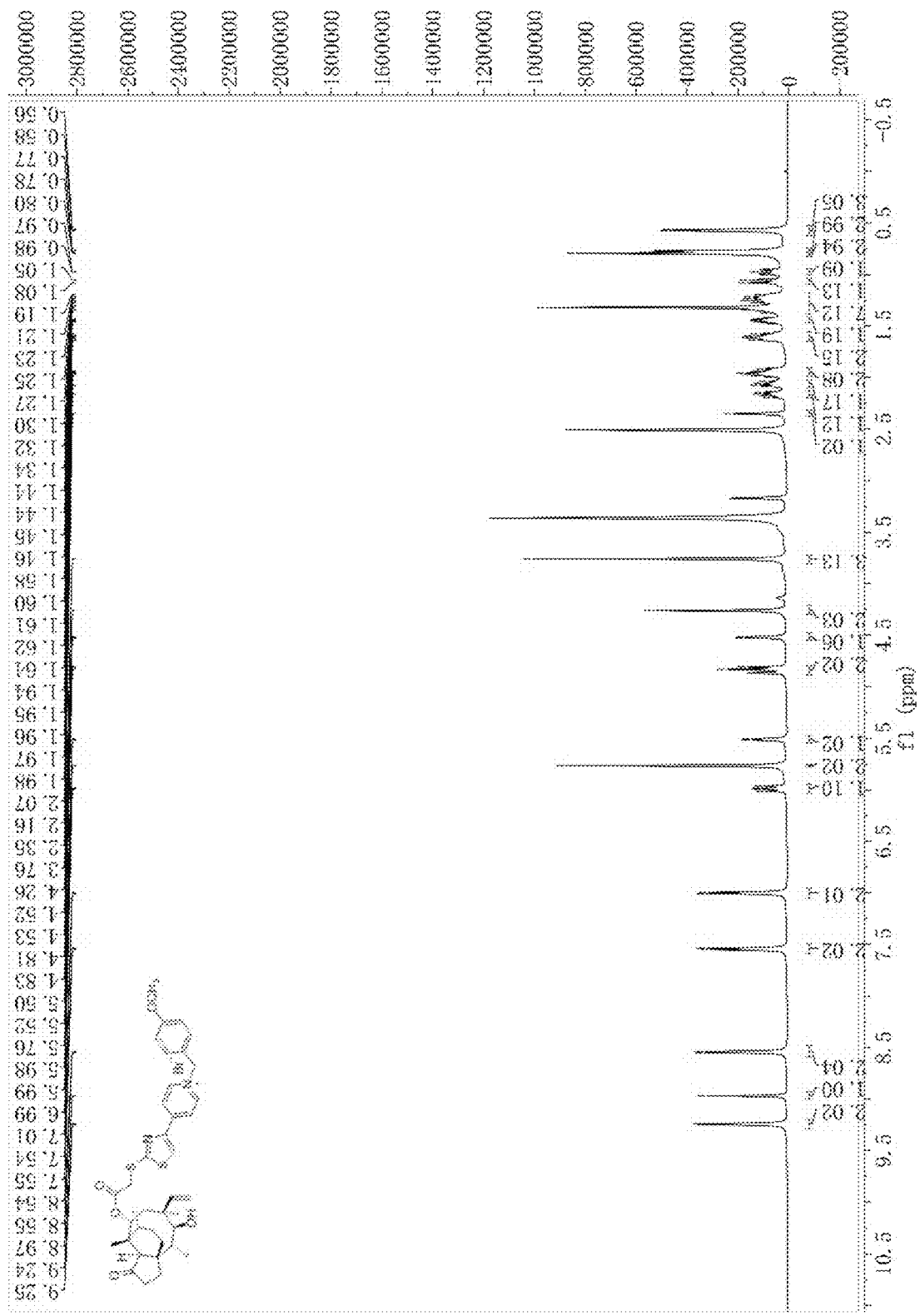
FIG. 7 is the H NMR spectrum of compound 4 in deuterated DMSO in the present invention.
Figure 8:
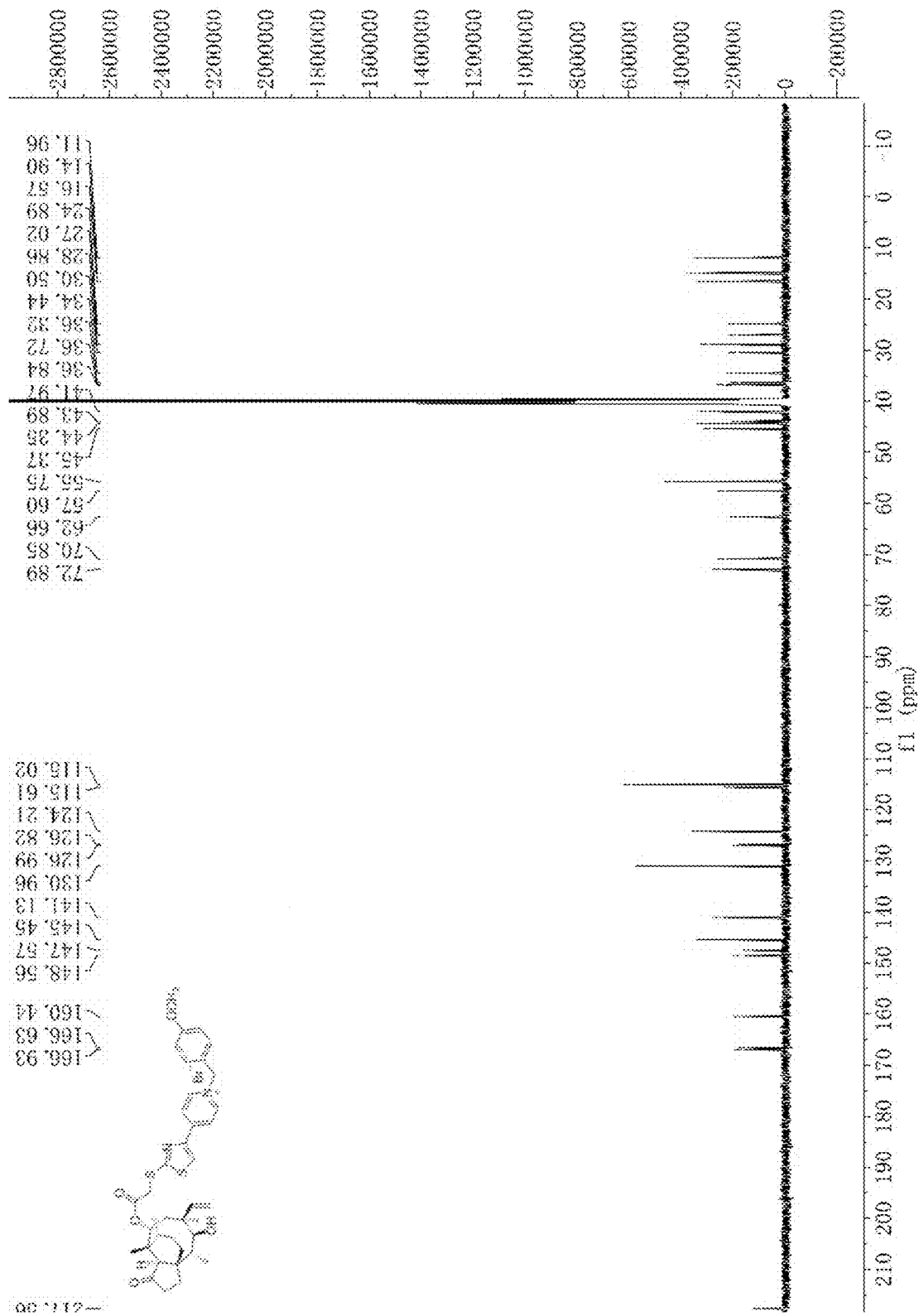
FIG. 8 is the C NMR spectrum of compound 4 in deuterated DMSO in the present invention.

The preparation method of intermediate I and intermediate II is the same as in Example 1. 166.4 mg (0.3 mmol) of intermediate II and 120.7 mg (0.6 mmol) of 4-methoxybenzyl bromide were placed in a reactor, dissolved in 5 mL of acetonitrile, stirred overnight at room temperature, and monitored by TLC. After the reaction, the reaction mixture was concentrated under reduced pressure to remove acetonitrile, separated and purified by column chromatography (dichloromethane:methanol (V:V)=10:1), and dried to obtain 178.9 mg of compound 4 with a yield of 78.89%. The H NMR spectrum of compound 4 in deuterated DMSO is shown in FIG. 7, and the C NMR spectrum in deuterated DMSO is shown in FIG. 8.

$^1$H NMR (600 MHz, DMSO) δ 9.24 (d, J=6.4 Hz, 2H), 8.97 (s, 1H), 8.55 (d, J=6.3 Hz, 2H), 7.54 (d, J=8.3 Hz, 2H), 7.00 (d, J=8.3 Hz, 2H), 5.99 (dd, J=17.8, 11.1 Hz, 1H), 5.76 (s, 2H), 5.51 (d, J=8.4 Hz, 1H), 4.82 (d, J=12.6 Hz, 2H), 4.52 (d, J=6.0 Hz, 1H), 4.26 (s, 2H), 3.76 (s, 3H), 2.35 (s, 1H), 2.17 (dd, J=19.2, 10.9 Hz, 1H), 2.10-2.03 (m, 1H), 2.01-1.89 (m, 2H), 1.65-1.55 (m, 2H), 1.50-1.41 (m, 1H), 1.38-1.18 (m, 7H), 1.06 (d, J=15.8 Hz, 1H), 1.02-0.93 (m, 1H), 0.80 (s, 3H), 0.77 (d, J=7.0 Hz, 3H), 0.57 (d, J=7.1 Hz, 3H).

$^{13}$C NMR (151 MHz, DMSO) δ 217.56, 166.93, 166.63, 160.44, 148.56, 147.57, 145.45, 141.13, 130.96, 126.99, 126.82, 124.21, 115.61, 115.02, 72.89, 70.85, 62.66, 57.60, 55.75, 45.37, 44.35, 43.89, 41.97, 36.84, 36.72, 36.32, 34.44, 30.50, 28.86, 27.02, 24.89, 16.57, 14.90, 11.96.

Figure 9:
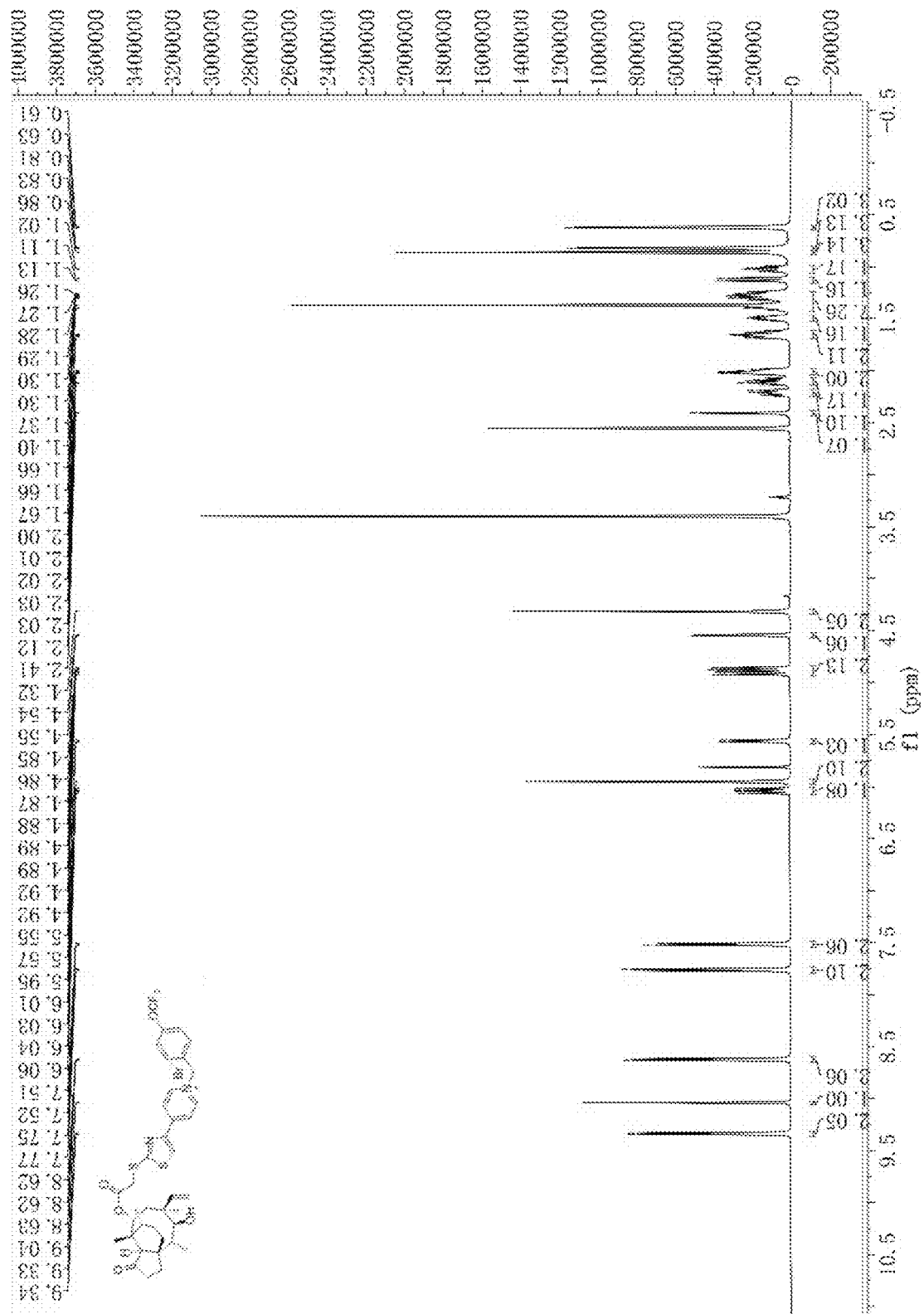
FIG. 9 is the H NMR spectrum of compound 5 in deuterated DMSO in the present invention.
Figure 10:
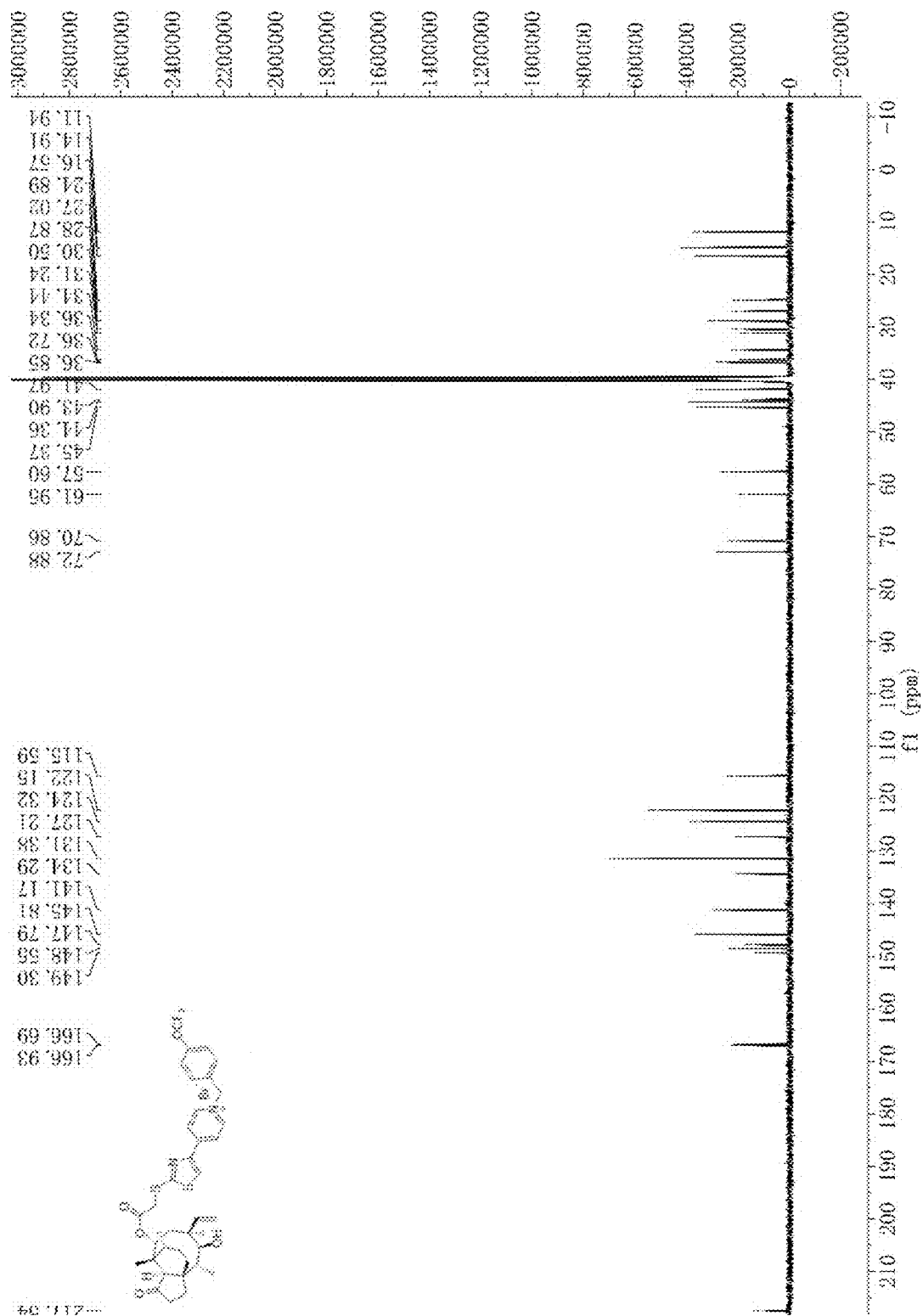
FIG. 10 is the C NMR spectrum of compound 5 in deuterated DMSO in the present invention.

The preparation method of intermediate I and intermediate II is the same as in Example 1. 166.4 mg (0.3 mmol) of intermediate II and 153.0 mg (0.6 mmol) of p-trifluoromethoxybenzyl bromide were placed in a reactor, dissolved in 5 mL of toluene, stirred overnight at room temperature, and monitored by TLC. After the reaction, the reaction mixture was concentrated under reduced pressure to remove toluene, separated and purified by column chromatography (dichloromethane:methanol (V:V)=10:1), and dried to obtain 183.9 mg of compound 5 with a yield of 75.69%. The H NMR spectrum of compound 5 in deuterated DMSO is shown in FIG. 9, and the C NMR spectrum in deuterated DMSO is shown in FIG. 10.

$^1$H NMR (600 MHz, DMSO) δ 9.34 (d, J=6.6 Hz, 2H), 9.04 (s, 1H), 8.65-8.60 (m, 2H), 7.76 (d, J=8.7 Hz, 2H), 7.51 (d, J=8.3 Hz, 2H), 6.04 (dd, J=17.7, 11.2 Hz, 1H), 5.95 (s, 2H), 5.56 (d, J=8.3 Hz, 1H), 4.94-4.84 (m, 2H), 4.54 (d, J=6.0 Hz, 1H), 4.32 (s, 2H), 2.41 (s, 1H), 2.22 (dd, J=19.7, 10.5 Hz, 1H), 2.14-2.07 (m, 1H), 2.05-1.98 (m, 2H), 1.70-1.61 (m, 2H), 1.54-1.45 (m, 1H), 1.42-1.23 (m, 7H), 1.12 (d, J=15.8 Hz, 1H), 1.05-0.99 (m, 1H), 0.86 (s, 3H), 0.82 (d, J=7.0 Hz, 3H), 0.62 (d, J=7.1 Hz, 3H).

$^{13}$C NMR (151 MHz, DMSO) δ 217.54, 166.93, 166.69, 149.30, 148.55, 147.79, 145.81, 141.17, 134.29, 131.38, 127.21, 124.32, 122.15, 115.59, 72.88, 70.86, 61.95, 57.60, 45.37, 44.36, 43.90, 41.97, 36.85, 36.72, 36.34, 34.44, 31.24, 30.50, 28.87, 27.02, 24.89, 16.57, 14.91, 11.94.

Example 5

Compound 5: Preparation of 1-(4-(trifluoromethoxy)benzyl)-4-(2-(8-hydroxy-4,7,9,12-tetramethyl-3-oxo-7-vinyldecahydro-4,9a-propancyclopent[8]cyclen-5-yl)oxy)-2-oxoethyl)thiazol-4-yl)pyridyl bromide salt Example 6

Compound 6: Preparation of 1-(4-(tert-butyl)benzyl)-4-(2-(8-hydroxy-4,7,9,12-tetramethyl-3-oxo-7-vinyldecahydro-4,9a-propancyclopent[8]cyclen-5-yl)oxy)-2-oxoethyl)thiazol-4-yl)pyridyl bromide salt

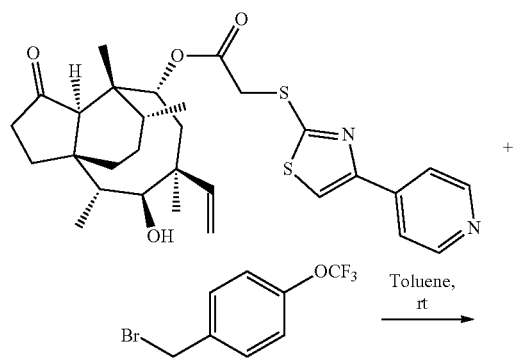

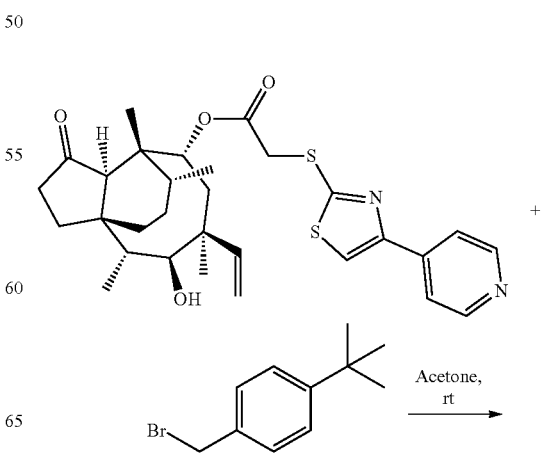

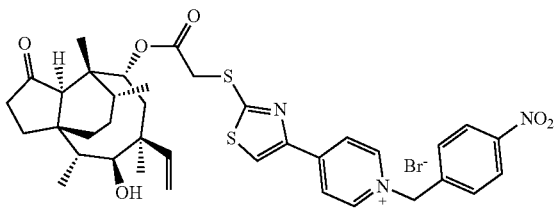

Figure 11:
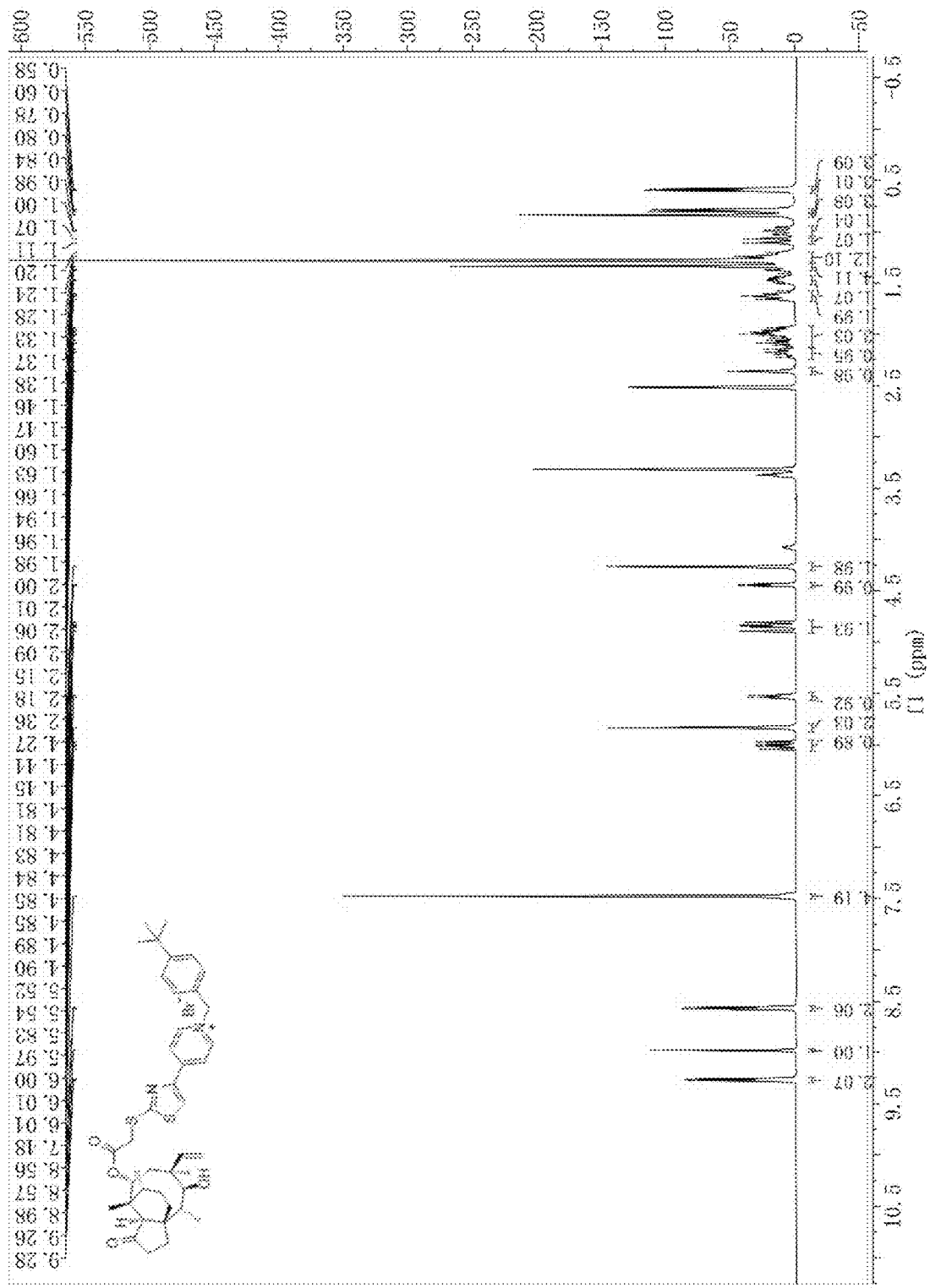
FIG. 11 is the H NMR spectrum of compound 6 in deuterated DMSO in the present invention.
Figure 12:
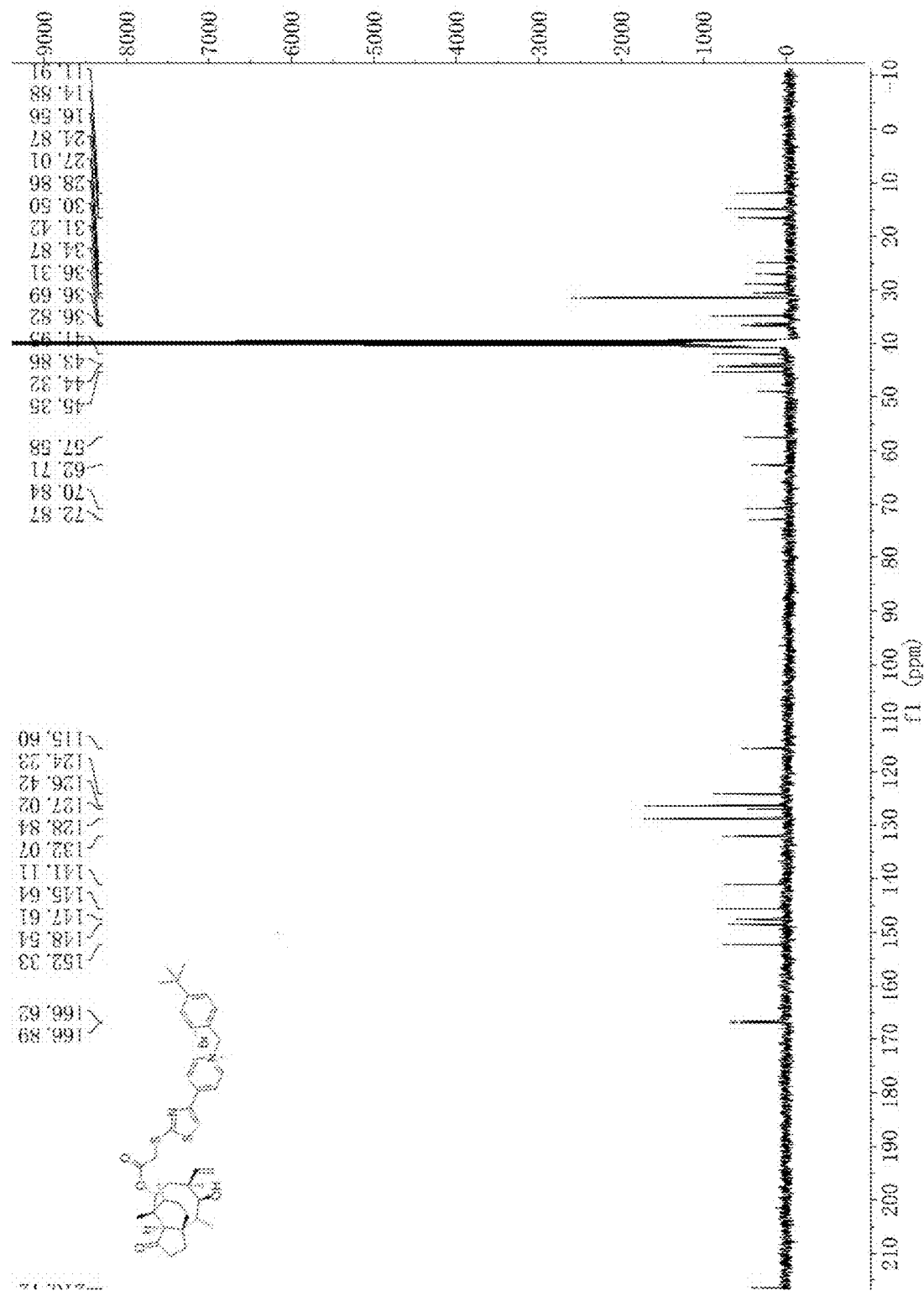
FIG. 12 is the C NMR spectrum of compound 6 in deuterated DMSO in the present invention.

The preparation method of intermediate I and intermediate II is the same as in Example 1. 166.4 mg (0.3 mmol) of intermediate II and 136.3 mg (0.6 mmol) of p-tert-butylbenzyl bromide were placed in a reactor, dissolved in 5 mL of acetone, stirred overnight at room temperature, and monitored by TLC. After the reaction, the reaction mixture was concentrated under reduced pressure to remove acetone, separated and purified by column chromatography (dichloromethane:methanol (V:V)=10:1), and dried to obtain 170.1 mg of compound 6 with a yield of 72.51%. The H NMR spectrum of compound 6 in deuterated DMSO is shown in FIG. 11, and the C NMR spectrum in deuterated DMSO is shown in FIG. 12.

$^1$H NMR (400 MHz, DMSO) δ 9.27 (d, J=6.4 Hz, 2H), 8.98 (s, 1H), 8.57 (d, J=6.4 Hz, 2H), 7.48 (s, 4H), 6.01 (dd, J=17.8, 11.2 Hz, 1H), 5.83 (s, 2H), 5.53 (d, J=8.2 Hz, 1H), 4.97-4.73 (m, 2H), 4.45 (d, J=5.9 Hz, 1H), 4.27 (s, 2H), 2.36 (s, 1H), 2.19 (dd, J=19.1, 10.8 Hz, 1H), 2.12-1.93 (m, 3H), 1.69-1.57 (m, 2H), 1.52-1.42 (m, 1H), 1.42-1.31 (m, 4H), 1.31-1.19 (m, 12H), 1.09 (d, J=15.8 Hz, 1H), 1.04-0.94 (m, 1H), 0.84 (s, 3H), 0.79 (d, J=6.9 Hz, 3H), 0.59 (d, J=6.9 Hz, 3H).

$^{13}$C NMR (101 MHz, DMSO) δ 216.72, 166.89, 166.62, 152.33, 148.54, 147.61, 145.64, 141.11, 132.07, 128.84, 127.02, 126.42, 124.23, 115.60, 72.87, 70.84, 62.71, 57.58, 49.04, 45.35, 44.32, 43.86, 41.95, 36.82, 36.69, 36.31, 34.87, 31.42, 30.50, 28.86, 27.01, 24.87, 16.56, 14.88, 11.91.

Example 7

Figure 13:
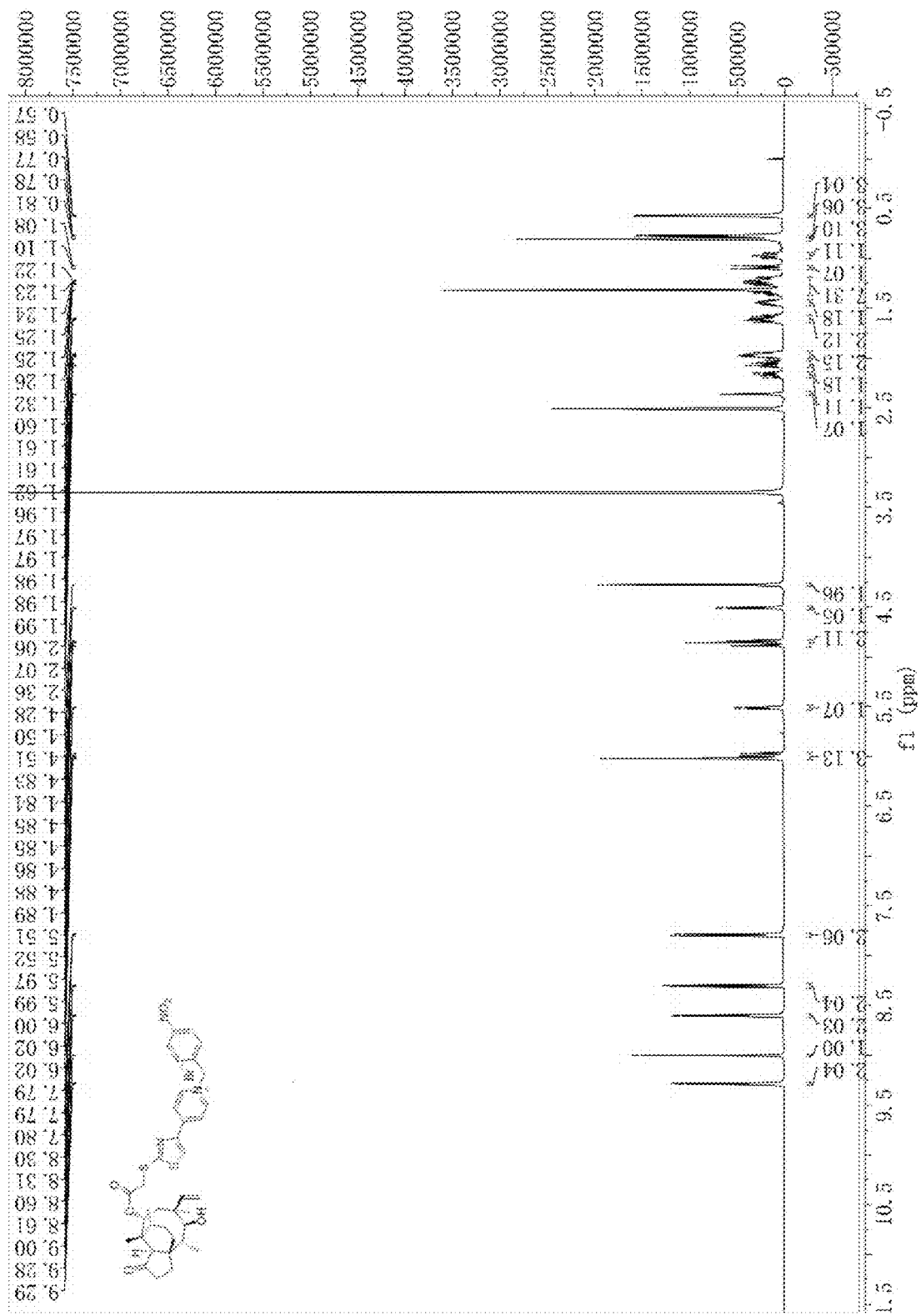
FIG. 13 is the H NMR spectrum of compound 7 in deuterated DMSO in the present invention.
Figure 14:
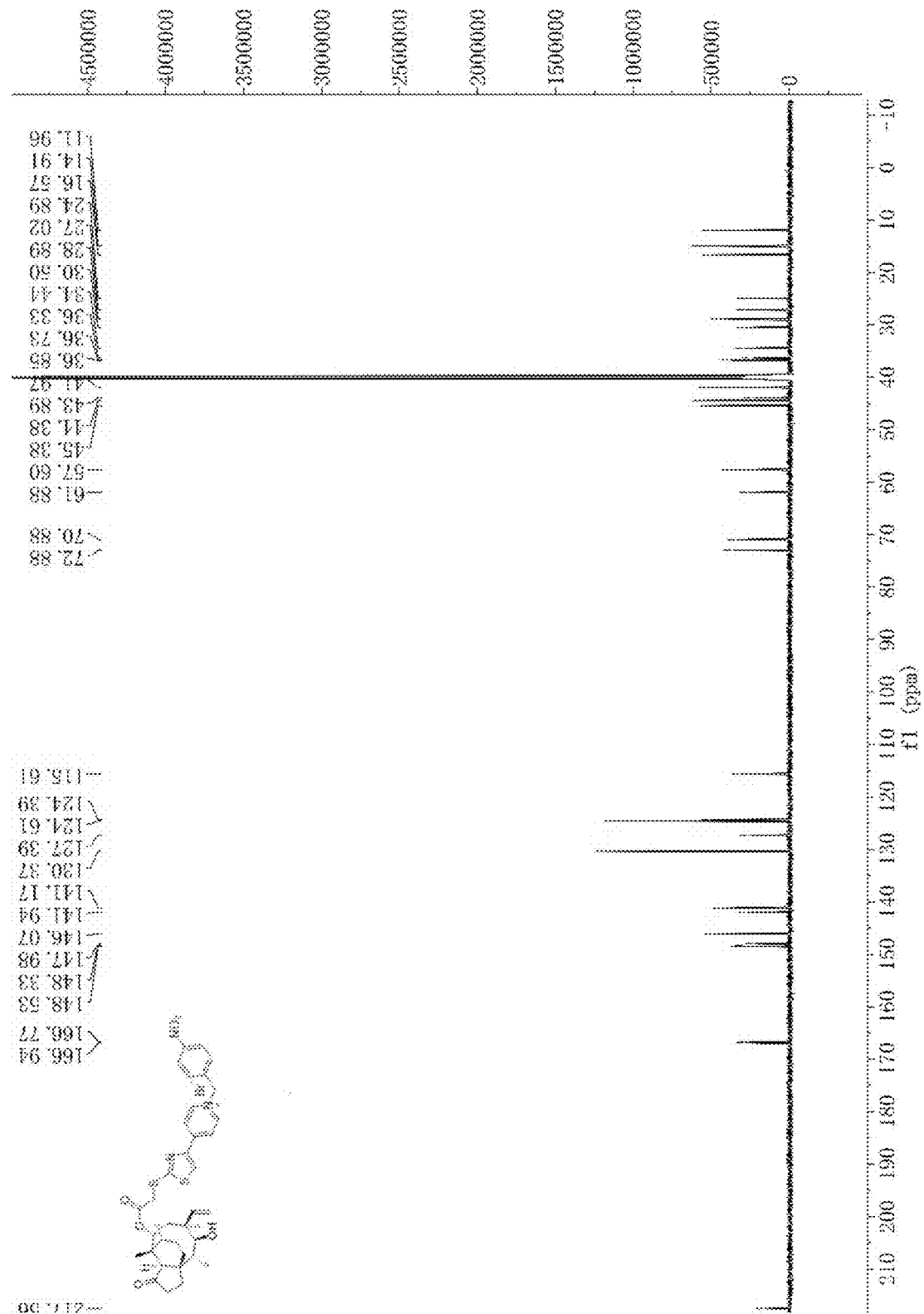
FIG. 14 is the C NMR spectrum of compound 7 in deuterated DMSO in the present invention.

Compound 7: Preparation of 1-(4-(nitro)benzyl)-4-(2-(8-hydroxy-4,7,9,12-tetramethyl-3-oxo-7-vinyl-decahydro-4,9a-propancyclopent[8]cyclen-5-yl)oxy)-2-oxoethyl)thiazol-4-yl)pyridyl bromide salt The preparation method of intermediate I and intermediate II is the same as in Example 1. 166.4 mg (0.3 mmol) of intermediate II and 194.4 mg (0.9 mmol) of p-nitrobenzyl bromide were placed in a reactor, dissolved in 5 mL of toluene, stirred overnight at room temperature, and monitored by TLC. After the reaction, the reaction mixture was concentrated under reduced pressure to remove toluene, separated and purified by column chromatography (dichloromethane:methanol (V:V)=10:1), and dried to obtain 179.2 mg of compound 7 with a yield of 77.51%. The H NMR spectrum of compound 7 in deuterated DMSO is shown in FIG. 13, and the C NMR spectrum in deuterated DMSO is shown in FIG. 14.

$^1$H NMR (600 MHz, DMSO) δ 9.29 (d, J=6.5 Hz, 2H), 9.00 (s, 1H), 8.60 (d, J=6.9 Hz, 2H), 8.30 (d, J=8.7 Hz, 2H), 7.79 (d, J=8.7 Hz, 2H), 6.09-5.94 (m, 3H), 5.52 (d, J=8.4 Hz, 1H), 4.90-4.82 (m, 2H), 4.51 (d, J=6.2 Hz, 1H), 4.28 (s, 2H), 2.36 (s, 1H), 2.17 (dd, J=19.2, 10.9 Hz, 1H), 2.10-2.02 (m, 1H), 2.00-1.94 (m, 2H), 1.66-1.55 (m, 2H), 1.49-1.40 (m, 1H), 1.38-1.19 (m, 7H), 1.09 (d, J=15.8 Hz, 1H), 1.02-0.93 (m, 1H), 0.81 (s, 3H), 0.78 (d, J=7.0 Hz, 3H), 0.57 (d, J=7.0 Hz, 3H).

$^{13}$C NMR (151 MHz, DMSO) δ 217.56, 166.94, 166.77, 148.53, 148.33, 147.98, 146.07, 141.94, 141.17, 130.37, 127.39, 124.61, 124.39, 115.61, 72.88, 70.88, 61.88, 57.60, 45.38, 44.38, 43.89, 41.97, 36.85, 36.73, 36.33, 34.44, 30.50, 28.89, 27.02, 24.89, 16.57, 14.91, 11.96.

Example 8

Compound 8: Preparation of 1-(4-(cyano)benzyl)-4-(2-(8-hydroxy-4,7,9,12-tetramethyl-3-oxo-7-vinyl-decahydro-4,9a-propancyclopent[8]cyclen-5-yl)oxy)-2-oxoethyl)thiazol-4-yl)pyridyl bromide salt

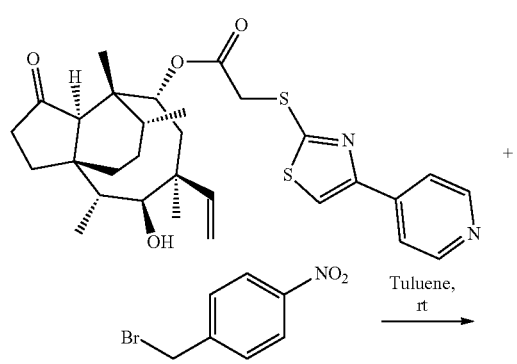

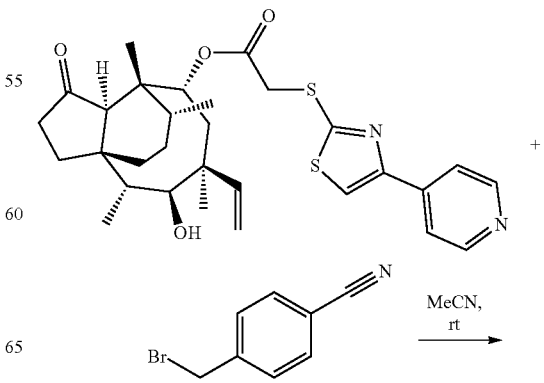

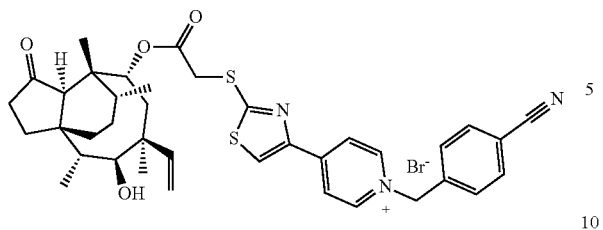

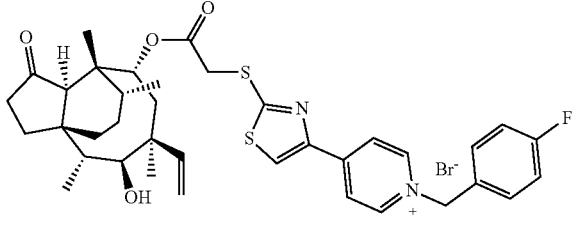

Figure 15:
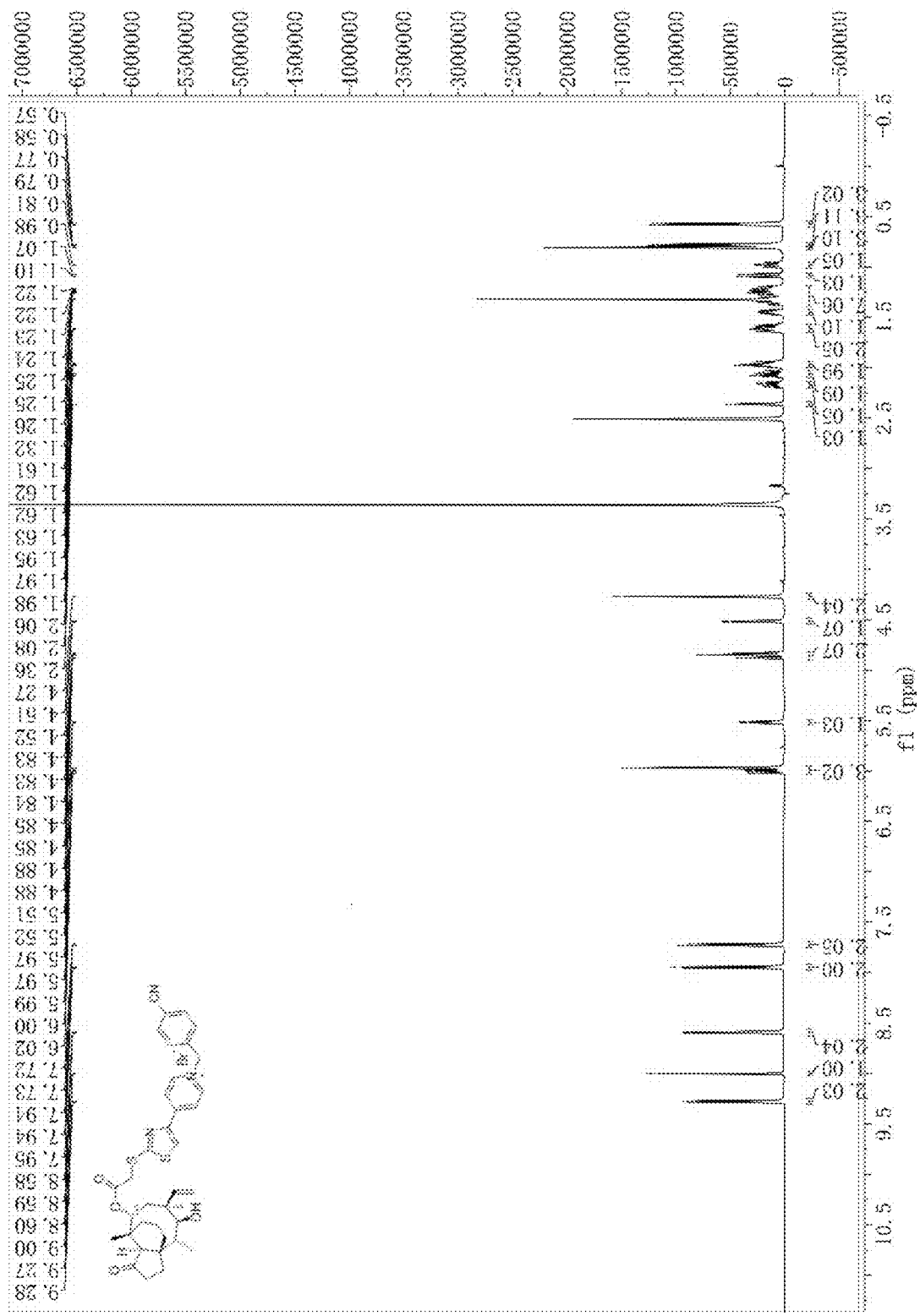
FIG. 15 is the H NMR spectrum of compound 8 in deuterated DMSO in the present invention.
Figure 16:
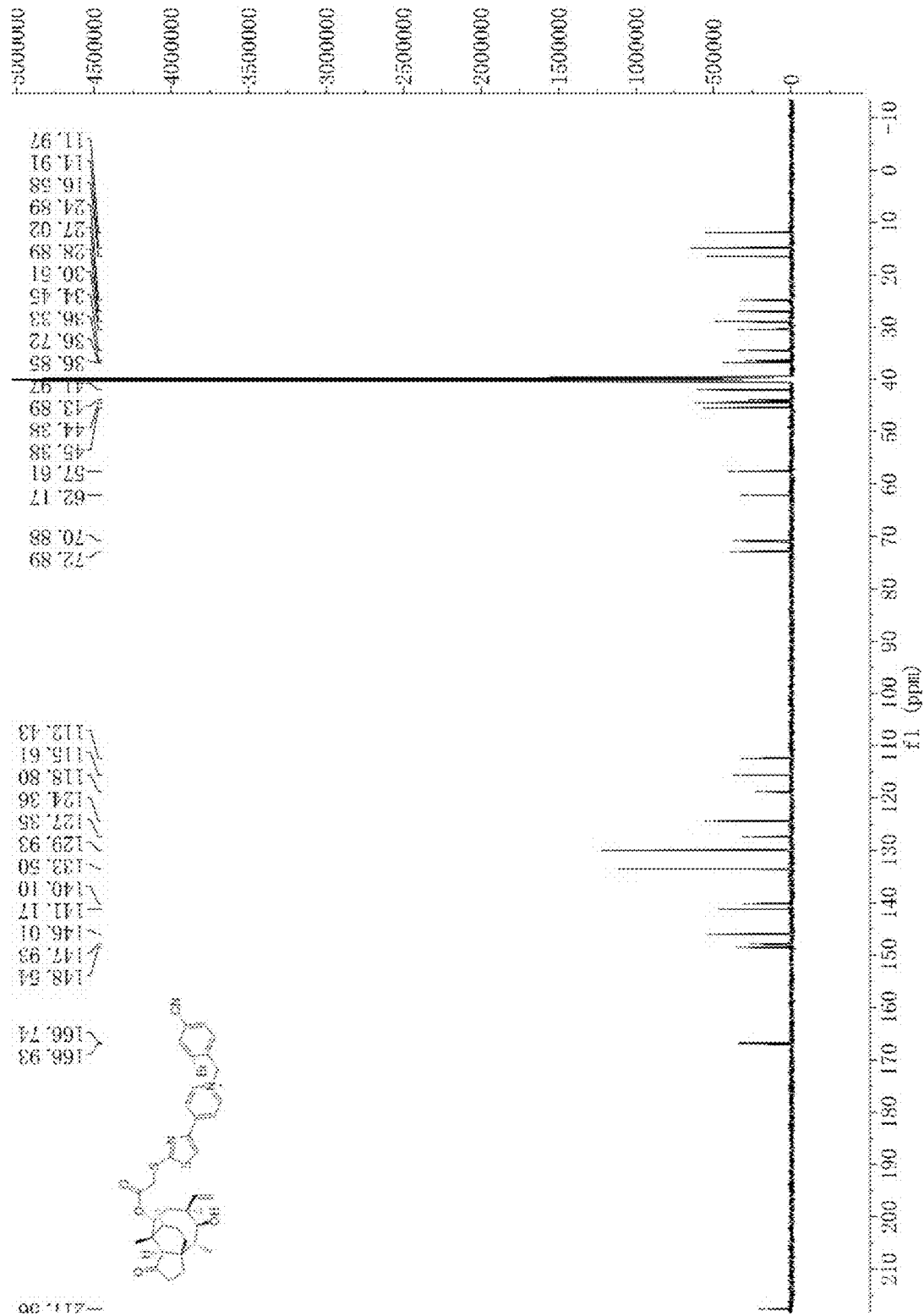
FIG. 16 is the C NMR spectrum of compound 8 in deuterated DMSO in the present invention.
Figure 17:
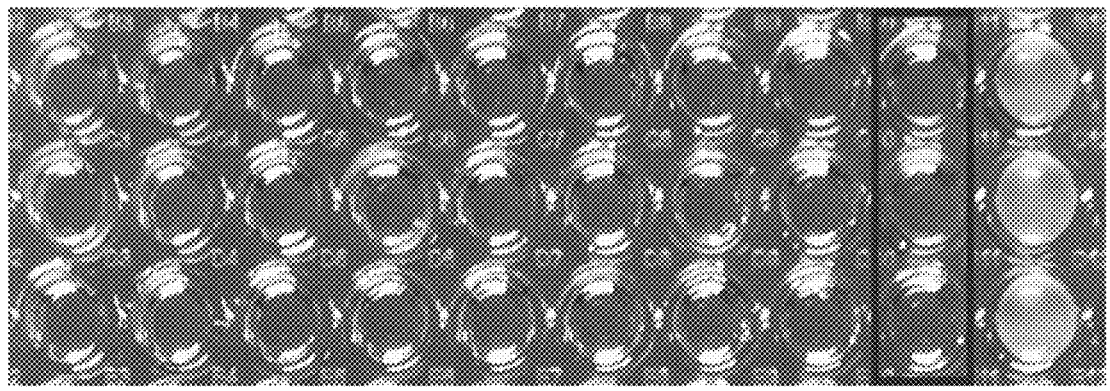
FIG. 17 is a graph showing the determination results of in vitro antibacterial activity of compound 2 against *Staphylococcus aureus* (ATCC 29213)
Figure 18:
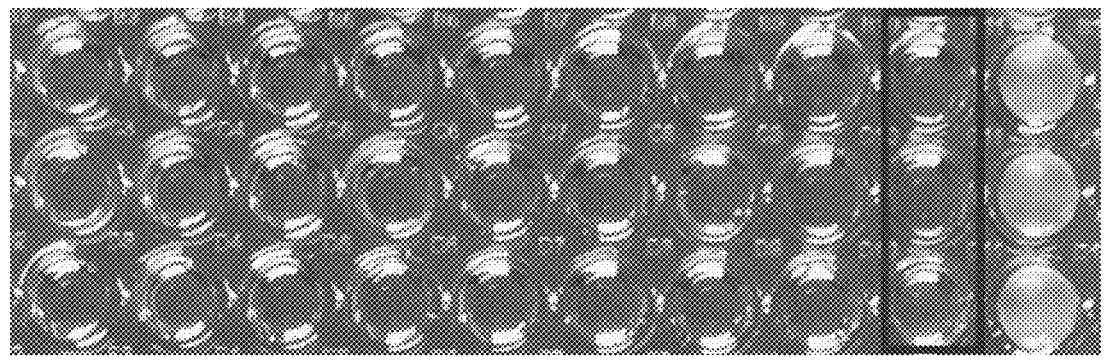
FIG. 18 is a graph showing the determination results of in vitro antibacterial activity of compound 2 against *Staphylococcus aureus* (ATCC 25923)
Figure 19:
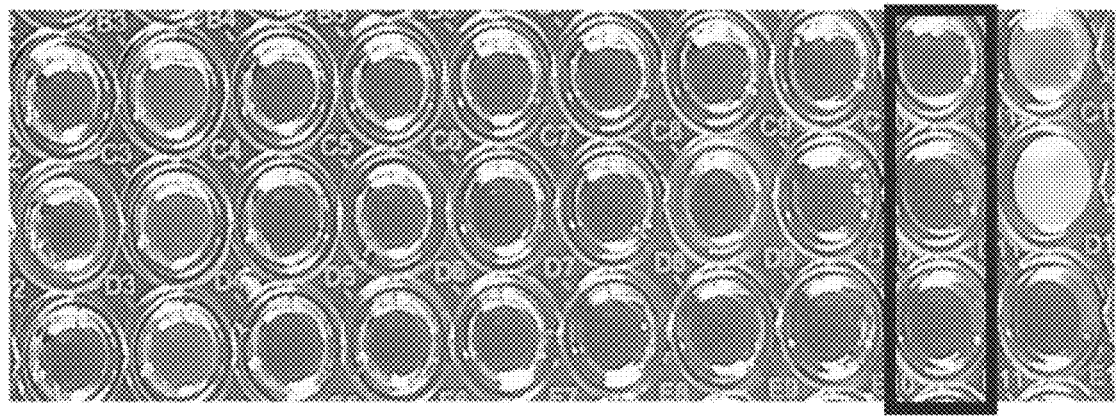
FIG. 19 is a graph showing the determination results of in vitro antibacterial activity of compound 2 against methicillin-resistant *Staphylococcus aureus* (ATCC 33591)
Figure 20:
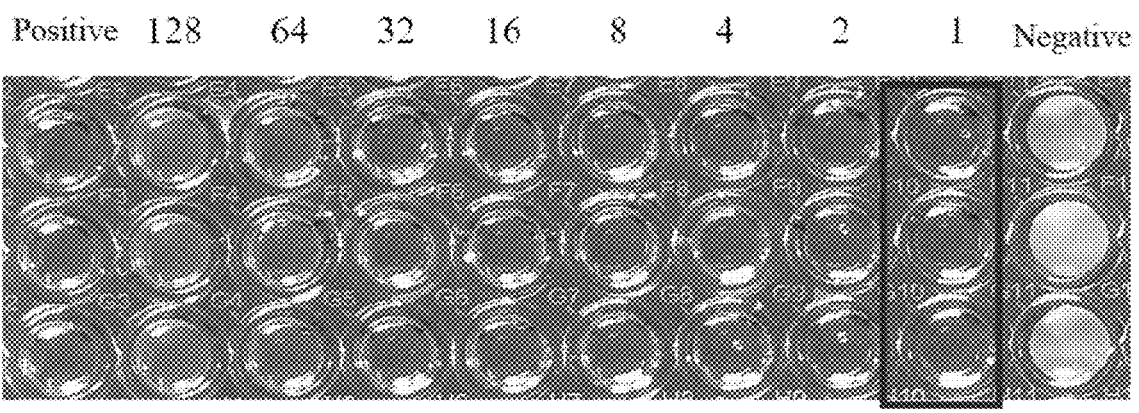
FIG. 20 is a graph showing the determination results of in vitro antibacterial activity of compound 2 against *Acinetobacter baumannii* (ATCC 19606)
Figure 21:
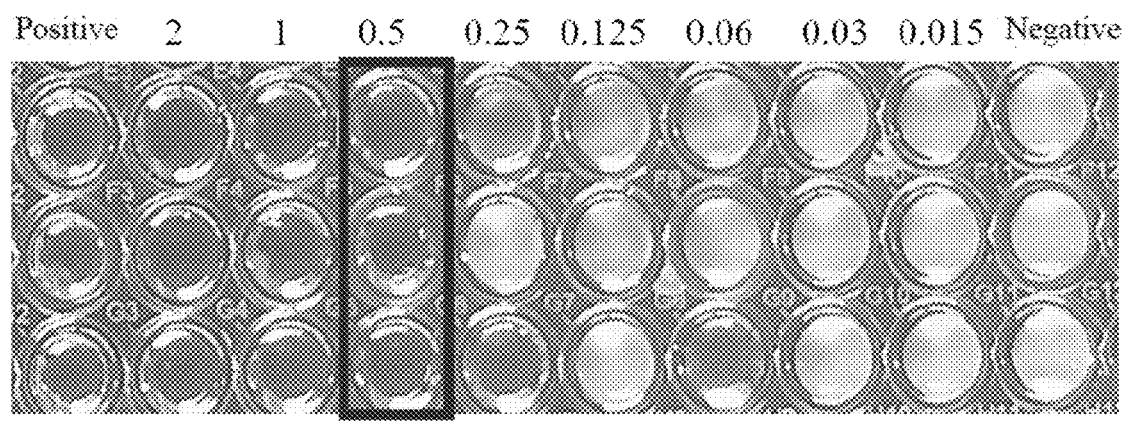
FIG. 21 is a graph showing the determination results of in vitro antibacterial activity of compound 2 against *Escherichia coli* (CMCC 44103)

The preparation method of intermediate I and intermediate II is the same as in Example 1. 166.4 mg (0.3 mmol) of intermediate II and 176.4 mg (0.9 mmol) of p-cyanobenzyl bromide were placed in a reactor, dissolved in 5 mL of acetonitrile, stirred overnight at room temperature, and monitored by TLC. After the reaction, the reaction mixture was concentrated under reduced pressure to remove acetonitrile, separated and purified by column chromatography (dichloromethane:methanol (V:V)=10:1), and dried to obtain 182.5 mg of compound 8 with a yield of 81.01%. The H NMR spectrum of compound 8 in deuterated DMSO is shown in FIG. 15, and the C NMR spectrum in deuterated DMSO is shown in FIG. 16.

$^1$H NMR (600 MHz, DMSO) δ 9.28 (d, J=6.5 Hz, 2H), 9.00 (s, 1H), 8.61-8.57 (m, 2H), 7.95 (d, J=8.2 Hz, 2H), 7.72 (d, J=8.1 Hz, 2H), 6.05-5.95 (m, 3H), 5.52 (d, J=8.3 Hz, 1H), 4.90-4.81 (m, 2H), 4.52 (d, J=6.0 Hz, 1H), 4.27 (s, 2H), 2.36 (s, 1H), 2.17 (dd, J=19.2, 10.9 Hz, 1H), 2.10-2.02 (m, 1H), 2.01-1.93 (m, 2H), 1.66-1.55 (m, 2H), 1.50-1.41 (m, 1H), 1.39-1.17 (m, 7H), 1.08 (d, J=15.8 Hz, 1H), 1.02-0.93 (m, 1H), 0.81 (s, 3H), 0.78 (d, J=7.0 Hz, 3H), 0.57 (d, J=7.0 Hz, 3H).

$^{13}$C NMR (151 MHz, DMSO) δ 217.56, 166.93, 166.74, 148.54, 147.93, 146.01, 141.17, 140.10, 133.50, 129.93, 127.35, 124.36, 118.80, 115.61, 112.43, 72.89, 70.88, 62.17, 57.61, 45.38, 44.38, 43.89, 41.97, 36.85, 36.72, 36.33, 34.45, 30.51, 28.89, 27.02, 24.89, 16.58, 14.91, 11.97.

Example 9

Compound 9: Preparation of 1-(4-fluorobenzyl)-4-(2-(8-hydroxy-4,7,9,12-tetramethyl-3-oxo-7-vinyl-decahydro-4,9a-propancyclopent[8]cyclen-5-yl)oxy)-2-oxoethyl)thiazol-4-yl)pyridyl bromide salt

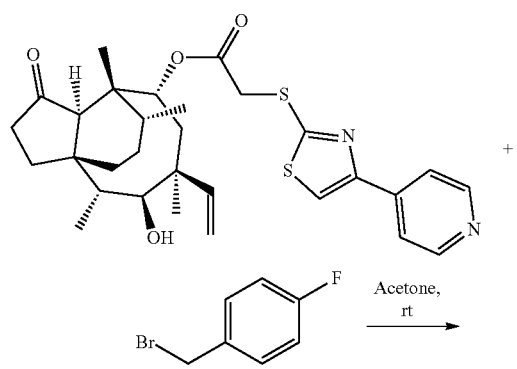

The preparation method of intermediate I and intermediate II is the same as in Example 1. 166.4 mg (0.3 mmol) of intermediate II and 170.1 mg (0.9 mmol) of p-fluorobenzyl bromide were placed in a reactor, dissolved in 5 mL of acetone, stirred overnight at room temperature, and monitored by TLC. After the reaction, the reaction mixture was concentrated under reduced pressure to remove acetone, separated and purified by column chromatography (dichloromethane:methanol (V:V)=10:1), and dried to obtain 175.7 mg of compound 9 with a yield of 78.73%.

$^1$H NMR (400 MHz, DMSO) δ 9.31 (d, J=6.3 Hz, 2H), 9.02 (s, 1H), 8.60 (d, J=6.2 Hz, 2H), 7.70 (t, J=6.8 Hz, 2H), 7.34 (t, J=8.6 Hz, 2H), 6.03 (dd, J=17.9, 11.2 Hz, 1H), 5.89 (s, 2H), 5.55 (d, J=8.1 Hz, 1H), 4.97-4.81 (m, 2H), 4.53 (d, J=5.8 Hz, 1H), 4.30 (s, 2H), 2.39 (s, 1H), 2.21 (dd, J=19.2, 11.0 Hz, 1H), 2.15-2.06 (m, 1H), 2.06-1.93 (m, 2H), 1.70-1.57 (m, 2H), 1.54-1.43 (m, 1H), 1.42-1.21 (m, 7H), 1.11 (d, J=15.4 Hz, 1H), 1.01 (t, J=13.4 Hz, 1H), 0.85-0.78 (m, 6H), 0.61 (d, J=6.8 Hz, 3H).

$^{13}$C NMR (101 MHz, DMSO) δ 216.71, 166.94, 166.68, 148.56, 147.72, 145.66, 141.15, 131.81, 131.73, 127.15, 124.28, 116.69, 116.47, 115.60, 72.90, 70.86, 62.13, 57.61, 45.38, 44.34, 43.91, 41.97, 36.84, 36.72, 36.34, 34.44, 30.51, 28.83, 27.03, 24.89, 16.58, 14.91, 11.96.

Example 10

Compound 10: Preparation of 1-(4-chlorobenzyl)-4-(2-(8-hydroxy-4,7,9,12-tetramethyl-3-oxo-7-vinyl-decahydro-4,9a-propancyclopent[8]cyclen-5-yl)oxy)-2-oxoethyl)thiazol-4-yl)pyridyl bromide salt

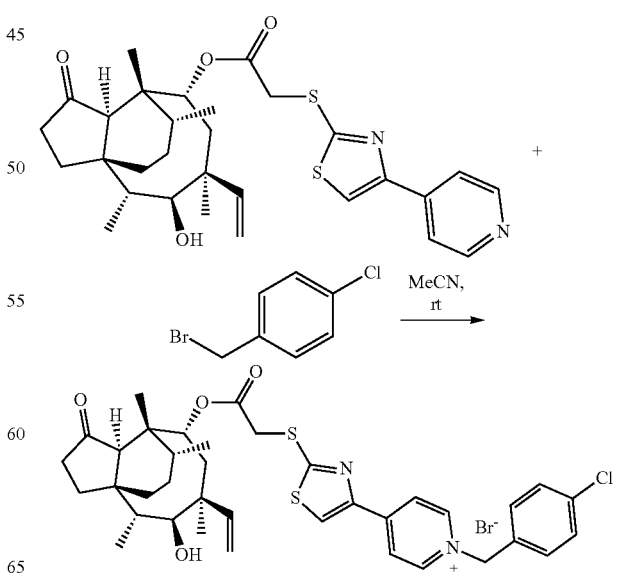

The preparation method of intermediate I and intermediate II is the same as in Example 1. 166.4 mg (0.3 mmol) of intermediate II and 369.9 mg (1.8 mmol) of p-chlorobenzyl bromide were placed in a reactor, dissolved in 5 mL of acetonitrile, stirred overnight at room temperature, and monitored by TLC. After the reaction, the reaction mixture was concentrated under reduced pressure to remove acetonitrile, separated and purified by column chromatography (dichloromethane:methanol (V:V)=10:1), and dried to obtain 203.4 mg of compound 10 with a yield of 89.19%.

$^1$H NMR (600 MHz, DMSO) δ 9.26 (d, J=6.5 Hz, 2H), 8.98 (s, 2H), 8.57 (d, J=6.8 Hz, 1H), 7.60 (d, J=8.3 Hz, 2H), 7.53 (d, J=8.5 Hz, 2H), 6.00 (dd, J=17.7, 11.2 Hz, 1H), 5.86 (s, 2H), 5.52 (d, J=8.3 Hz, 1H), 4.95-4.79 (m, 2H), 4.51 (d, J=6.0 Hz, 1H), 4.27 (s, 2H), 2.36 (s, 1H), 2.17 (dd, J=18.9, 11.2 Hz, 1H), 2.11-2.01 (m, 1H), 2.01-1.92 (m, 2H), 1.66-1.56 (m, 2H), 1.50-1.41 (m, 1H), 1.40-1.18 (m, 7H), 1.08 (d, J=15.7 Hz, 1H), 1.02-0.93 (m, 1H), 0.82 (s, 3H), 0.78 (d, J=6.9 Hz, 3H), 0.58 (d, J=7.0 Hz, 3H).

$^{13}$C NMR (151 MHz, DMSO) δ 217.55, 166.93, 166.69, 148.54, 147.77, 145.75, 141.16, 134.60, 133.84, 131.17, 129.64, 127.19, 124.28, 115.61, 72.90, 70.87, 62.10, 57.61, 49.06, 45.38, 44.36, 43.91, 41.97, 36.84, 36.72, 34.45, 30.51, 28.88, 27.02, 24.89, 16.58, 14.91, 11.96.

Example 11

Compound 11: Preparation of 1-(4-bromobenzyl)-4-(2-(8-hydroxy-4,7,9,12-tetramethyl-3-oxo-7-vinyl-decahydro-4,9a-propancyclopent[8]cyclen-5-yl)oxy)-2-oxoethyl)thiazol-4-yl)pyridyl bromide salt

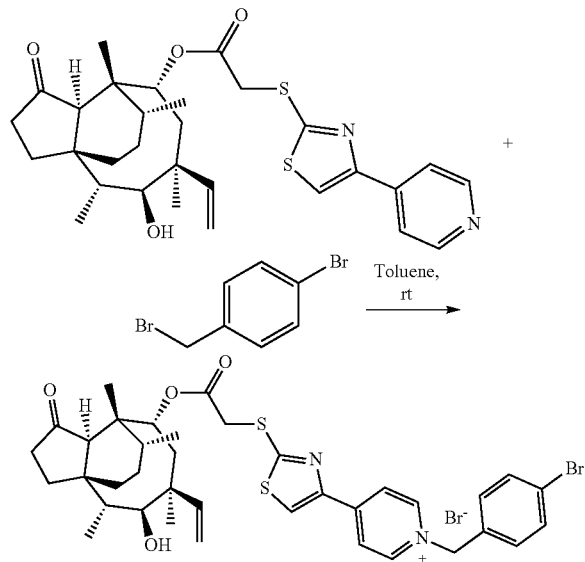

The preparation method of intermediate I and intermediate II is the same as in Example 1. 166.4 mg (0.3 mmol) of intermediate II and 449.9 mg (1.8 mmol) of p-bromobenzyl bromide were placed in a reactor, dissolved in 5 mL of toluene, stirred overnight at room temperature, and monitored by TLC. After the reaction, the reaction mixture was concentrated under reduced pressure to remove toluene, separated and purified by column chromatography (dichloromethane:methanol=10:1), and dried to obtain 201.0 mg of compound 11 with a yield of 83.26%.

$^1$H NMR (600 MHz, DMSO) δ 9.25 (d, J=6.9 Hz, 2H), 8.98 (s, 1H), 8.57 (d, J=6.9 Hz, 2H), 7.67 (d, J=8.4 Hz, 2H), 7.52 (d, J=8.5 Hz, 2H), 6.00 (dd, J=17.7, 11.2 Hz, 1H), 5.83 (s, 2H), 5.52 (d, J=8.4 Hz, 1H), 4.90-4.81 (m, 2H), 4.51 (d, J=6.0 Hz, 1H), 4.27 (s, 2H), 2.38-2.35 (m, 1H), 2.21-2.13 (m, 1H), 2.11-2.01 (m, 1H), 2.01-1.93 (m, 2H), 1.66-1.55 (m, 2H), 1.50-1.41 (m, 1H), 1.39-1.18 (m, 7H), 1.08 (d, J=15.9 Hz, 1H), 1.02-0.94 (m, 1H), 0.82 (s, 3H), 0.78 (d, J=6.9 Hz, 3H), 0.57 (d, J=7.0 Hz, 3H).

$^{13}$C NMR (151 MHz, DMSO) δ 217.56, 166.94, 166.70, 148.55, 147.78, 145.76, 141.17, 134.24, 132.58, 131.41, 127.19, 124.28, 123.26, 115.61, 72.90, 70.87, 62.18, 57.61, 45.38, 44.37, 43.91, 41.97, 36.85, 36.73, 36.34, 34.45, 30.51, 28.89, 27.02, 24.90, 16.58, 14.91, 11.97.

Example 12

Compound 12: Preparation of 1-([1,1'-biphenyl]-4-ylmethyl)-4-(2-(8-hydroxy-4,7,9,12-tetramethyl-3-oxo-7-vinyldecahydro-4,9a-propancyclopent[8]cyclen-5-yl)oxy)-2-oxoethyl)thiazol-4-yl)pyridyl bromide salt

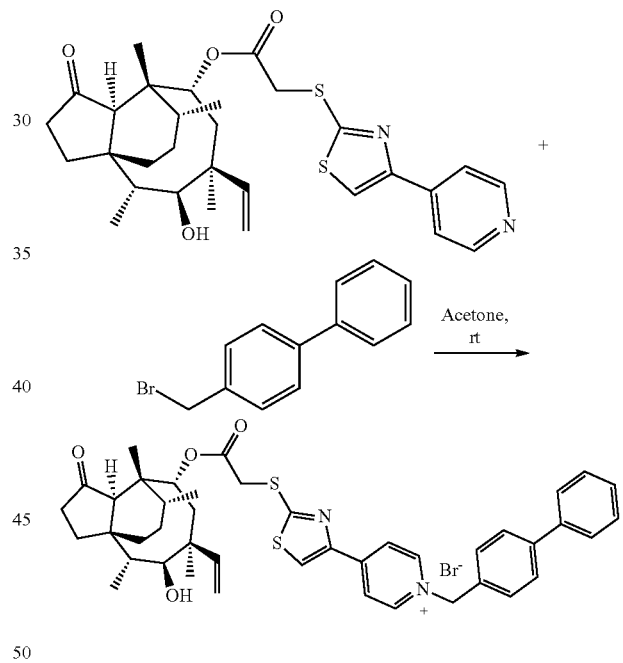

The preparation method of intermediate I and intermediate II is the same as in Example 1. 166.4 mg (0.3 mmol) of intermediate II and 444.9 mg (1.8 mmol) of 4-bromomethylbiphene were placed in a reactor, dissolved in 5 mL of acetone, stirred overnight at room temperature, and monitored by TLC. After the reaction, the reaction mixture was concentrated under reduced pressure to remove acetone, separated and purified by column chromatography (dichloromethane:methanol (V:V)=10:1), and dried to obtain 197.6 mg of compound 12 with a yield of 82.14%.

$^1$H NMR (400 MHz, DMSO) δ 9.33 (d, J=6.5 Hz, 2H), 9.01 (s, 1H), 8.61 (d, J=6.4 Hz, 2H), 7.77 (d, J=8.0 Hz, 2H), 7.68 (dd, J=11.5, 7.9 Hz, 4H), 7.50 (t, J=7.6 Hz, 2H), 7.41 (t, J=7.3 Hz, 1H), 6.03 (dd, J=17.8, 11.2 Hz, 1H), 5.94 (s, 2H), 5.55 (d, J=8.2 Hz, 1H), 4.96-4.83 (m, 2H), 4.47 (d, J=5.9 Hz, 1H), 4.29 (s, 2H), 2.37 (s, 1H), 2.25-2.13 (m, 1H), 2.13-1.93 (m, 3H), 1.69-1.55 (m, 2H), 1.53-1.44 (m, 1H), 1.42-1.19 (m, 7H), 1.12 (d, J=15.8 Hz, 1H), 1.05-0.93 (m, 1H), 0.87 (s, 3H), 0.80 (d, J=6.9 Hz, 3H), 0.60 (d, J=6.9 Hz, 3H).

$^{13}$C NMR (101 MHz, DMSO) δ 216.32, 166.94, 166.68, 148.59, 147.74, 145.78, 141.58, 141.17, 139.74, 134.06, 129.77, 129.49, 128.35, 127.91, 127.29, 127.14, 124.31, 115.64, 72.91, 70.88, 62.69, 57.61, 45.37, 44.38, 43.90, 41.98, 36.84, 36.72, 36.34, 34.44, 30.51, 28.91, 27.02, 24.90, 16.58, 14.91, 11.95.

Example 13

Compound 13: Preparation of 1-(3,5-dimethylbenzyl)-4-(2-(8-hydroxy-4,7,9,12-tetramethyl-3-oxo-7-vinyldecahydro-4,9a-propancyclopent[8]cyclen-5-yl)oxy)-2-oxoethyl)thiazol-4-yl)pyridyl bromide salt

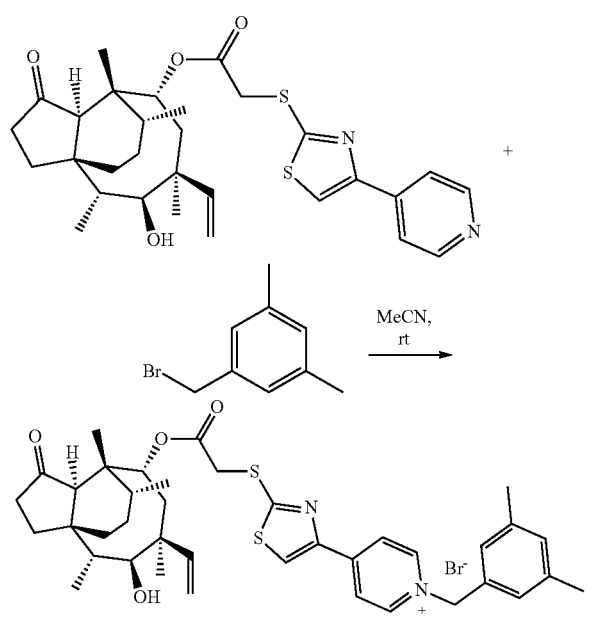

The preparation method of intermediate I and intermediate II is the same as in Example 1. 166.4 mg (0.3 mmol) of intermediate II and 298.6 mg (1.5 mmol) of 3,5-dimethylbenzyl bromide were placed in a reactor, dissolved in 5 mL of acetonitrile, stirred overnight at room temperature, and monitored by TLC. After the reaction, the reaction mixture was concentrated under reduced pressure to remove acetonitrile, separated and purified by column chromatography (dichloromethane:methanol (V:V)=10:1), and dried to obtain 189.9 mg of compound 13 with a yield of 83.95%.

$^{1}$H NMR (400 MHz, DMSO) δ 9.29 (d, J=6.4 Hz, 2H), 9.05 (s, 1H), 8.59 (d, J=6.3 Hz, 2H), 7.17 (s, 2H), 7.07 (s, 1H), 6.01 (dd, J=17.7, 11.1 Hz, 1H), 5.80 (s, 2H), 5.53 (d, J=8.2 Hz, 1H), 4.91-4.81 (m, 2H), 4.53 (d, J=5.9 Hz, 1H), 4.28 (s, 2H), 2.37 (s, 1H), 2.29 (s, 6H), 2.19 (dd, J=19.1, 10.8 Hz, 1H), 2.12-1.92 (m, 3H), 1.68-1.56 (m, 2H), 1.52-1.43 (m, 1H), 1.41-1.20 (m, 7H), 1.08 (d, J=15.7 Hz, 1H), 1.04-0.94 (m, 1H), 0.83-0.76 (m, 6H), 0.60 (d, J=6.8 Hz, 3H).

$^{13}$C NMR (101 MHz, DMSO) δ 216.53, 166.92, 166.60, 148.55, 147.60, 145.70, 141.17, 138.89, 134.82, 131.06, 127.15, 126.69, 124.21, 115.57, 72.86, 70.84, 62.94, 57.59, 45.35, 44.32, 43.89, 41.95, 36.83, 36.70, 36.32, 34.43, 30.51, 28.80, 27.02, 24.87, 21.29, 16.58, 14.89, 11.95.

Example 14

Compound 14: Preparation of 1-(3,5-dimethoxybenzyl)-4-(2-(8-hydroxy-4,7,9,12-tetramethyl-3-oxo-7-vinyldecahydro-4,9a-propancyclopent[8]cyclen-5-yl)oxy)-2-oxoethyl)thiazol-4-yl)pyridyl bromide salt

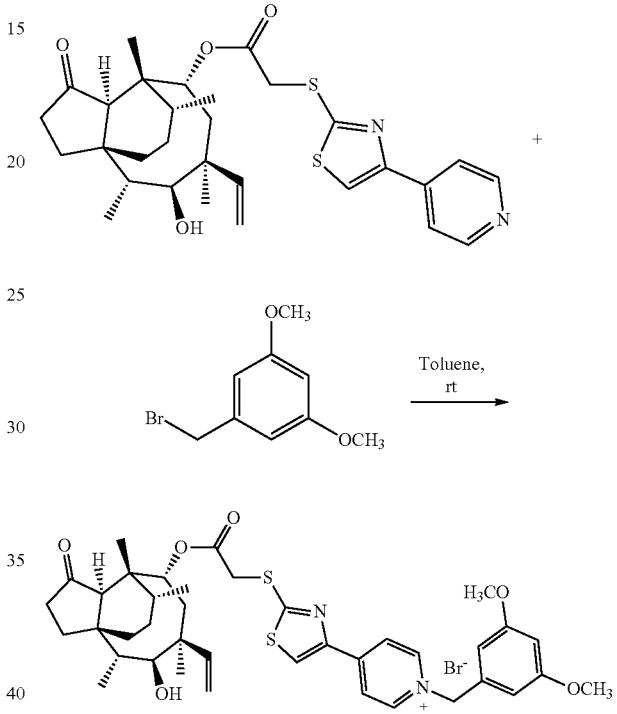

The preparation method of intermediate I and intermediate II is the same as in Example 1. 166.4 mg (0.3 mmol) of intermediate II and 346.6 mg (1.5 mmol) of 3,5-dimethoxybenzyl bromide were placed in a reactor, dissolved in 5 mL of toluene, stirred overnight at room temperature, and monitored by TLC. After the reaction, the reaction mixture was concentrated under reduced pressure to remove toluene, separated and purified by column chromatography (dichloromethane:methanol (V:V)=10:1), and dried to obtain 194.5 mg of compound 14 with a yield of 82.51%.

$^{1}$H NMR (400 MHz, DMSO) δ 9.34 (d, J=6.3 Hz, 2H), 9.03 (s, 1H), 8.58 (d, J=6.3 Hz, 2H), 6.82 (d, J=2.2 Hz, 2H), 6.56 (d, J=2.3 Hz, 1H), 6.02 (dd, J=17.7, 11.2 Hz, 1H), 5.77 (s, 2H), 5.54 (d, J=8.2 Hz, 1H), 4.93-4.81 (m, 2H), 4.53 (d, J=5.9 Hz, 1H), 4.29 (s, 2H), 3.78 (s, 6H), 2.37 (s, 1H), 2.20 (dd, J=19.2, 10.8 Hz, 1H), 2.14-1.93 (m, 3H), 1.69-1.58 (m, 2H), 1.53-1.43 (m, 1H), 1.42-1.18 (m, 7H), 1.10 (d, J=15.9 Hz, 1H), 1.05-0.95 (m, 1H), 0.83 (s, 3H), 0.80 (d, J=7.0 Hz, 3H), 0.60 (d, J=6.9 Hz, 3H).

$^{13}$C NMR (101 MHz, DMSO) δ 216.61, 166.93, 166.60, 161.44, 148.57, 147.65, 145.69, 141.14, 136.85, 127.13, 124.16, 115.57, 107.39, 101.19, 72.86, 70.85, 62.93, 57.60, 55.90, 55.41, 45.36, 44.32, 43.92, 41.96, 36.84, 36.71, 34.46, 30.51, 28.79, 27.02, 24.88, 16.58, 14.90, 11.95.

Example 15

Compound 15: Preparation of 1-(3,5-difluorobenzyl)-4-(2-(8-hydroxy-4,7,9,12-tetramethyl-3-oxo-7-vinyldecahydro-4,9a-propancyclopent[8]cyclen-5-yl)oxy)-2-oxoethyl)thiazol-4-yl)pyridyl bromide salt

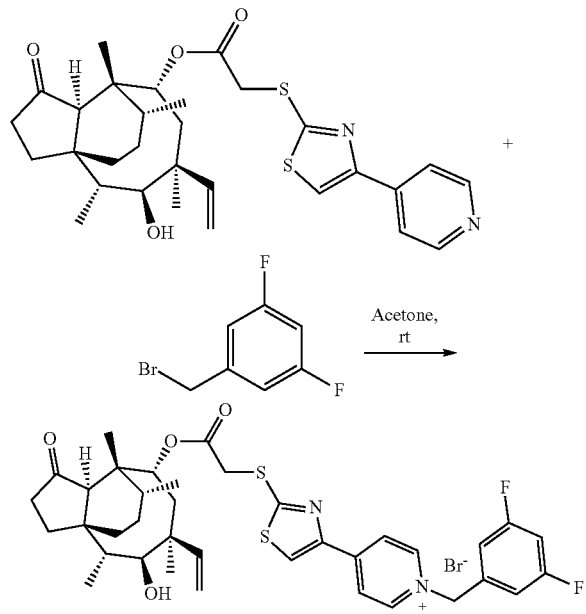

The preparation method of intermediate I and intermediate II is the same as in Example 1. 166.4 mg (0.3 mmol) of intermediate II and 310.5 mg (1.5 mmol) of 3,5-difluorobenzyl bromide were placed in a reactor, dissolved in 5 mL of acetone, stirred overnight at room temperature, and monitored by TLC. After the reaction, the reaction mixture was concentrated under reduced pressure to remove acetone, separated and purified by column chromatography (dichloromethane:methanol (V:V)=10:1), and dried to obtain 185.5 mg of compound 15 with a yield of 81.19%.

$^1$H NMR (600 MHz, DMSO) δ 9.29 (d, J=6.4 Hz, 2H), 9.00 (s, 1H), 8.60-8.56 (m, 2H), 7.41 (d, J=5.7 Hz, 2H), 7.38-7.33 (m, 1H), 5.99 (dd, J=17.7, 11.2 Hz, 1H), 5.87 (s, 2H), 5.51 (d, J=8.3 Hz, 1H), 4.90-4.78 (m, 2H), 4.50 (d, J=6.0 Hz, 1H), 4.27 (s, 2H), 2.36 (s, 1H), 2.17 (dd, J=19.1, 11.0 Hz, 1H), 2.10-2.01 (m, 1H), 1.99-1.89 (m, 2H), 1.66-1.56 (m, 2H), 1.50-1.41 (m, 1H), 1.38-1.18 (m, 7H), 1.07 (d, J=15.5 Hz, 1H), 1.01-0.93 (m, 1H), 0.79-0.75 (m, 6H), 0.58 (d, J=7.1 Hz, 3H).

$^{13}$C NMR (151 MHz, DMSO) δ 217.53, 166.94, 166.72, 162.78, 148.53, 147.90, 145.89, 141.17, 127.28, 124.32, 115.55, 112.91, 112.74, 72.87, 70.86, 61.62, 57.59, 45.37, 44.31, 43.91, 41.97, 36.84, 36.72, 36.26, 34.43, 31.24, 30.51, 28.77, 27.03, 24.89, 16.60, 14.91, 11.96.

2. IN VITRO ANTIBACTERIAL ACTIVITY ASSAY

The minimum inhibitory concentration (MIC) of the pleuromutilin derivative containing thiazole-pyridine benzyl quaternary ammonium salt side chain was tested with moxifloxacin as a positive control (purchased from Shanghai Macklin Biochemical Technology Co., Ltd.) using a micro-broth dilution method. At the same time, the pleuromutilin derivative containing thiazole-pyridine benzyl quaternary ammonium salt side chain of the invention was compared with the marketed pleuromutilin antibiotics, such as retapamulin (purchased from Nanjing Chemlin Chemical Industry Co., Ltd.), tiamulin (purchased from Shanghai Yuanye Bio-Technology Co., Ltd) and valnemulin (purchased from Shanghai Acmec Biochemical Co., Ltd), in order to screen out pleuromutilin derivatives with better activity.

Standard strains include gram-positive bacteria: *Staphylococcus epidermidis* ATCC 12228, *Staphylococcus aureus* ATCC 29213, ATCC 25923 and methicillin-resistant *Staphylococcus aureus* ATCC 33591; gram-negative bacteria: *Salmonella* ATCC 14028, *Acinetobacter baumannii* ATCC 19606, *Escherichia coli* ATCC 25922 and CMCC 44103, all the strains were purchased from the American Type Culture Collection.

Clinical resistant bacteria include multidrug-resistant *Pseudomonas aeruginosa* (MDR-PA) 18-993, 18-756 and 18-126, multidrug-resistant *Klebsiella pneumoniae* (MDR-KP) 18-893, 18-754 and 18-1482, methicillin-resistant *Staphylococcus aureus* (MRSA) 18-171, 18-209 and 18-575, vancomycin-resistant *Enterococcus faecalis* (VRE) 18-94, 18-80 and 18-507, and carbapenem-resistant *Acinetobacter baumannii* (CR-AB) 18-184, 18-560 and 18-882, all the clinical drug-resistant strains were from Huashan Hospital, Fudan University.

The specific operation steps are as follows:
(1) preparation of MHB medium: 20.0 g of MHB medium (purchased from Guangdong Huankai Microbial Sci. & Tech. Co., Ltd.) was weighed, added to 1 L of distilled water, heated and boiled until completely dissolved, dispensed into erlenmeyer flasks, and autoclaved at 121° C. for 15 minutes for later use.
(2) culture of the experimental strains to the logarithmic growth phase: under sterile conditions, the recovered experimental strains were inoculated into 100 mL of MHB medium, and placed in a constant temperature and humidity incubator at 37° C. for 20-22 h for later use.
(3) preparation of sample solutions: the samples to be tested (compounds 1-15 synthesized in the present invention, retapamulin, tiamulin, and valnemulin) were weighed and dissolved in DMSO solution to prepare sample solutions with a concentration of 10.24 mg/mL; the positive control (moxifloxacin) was dissolved in DMSO solution to prepare a sample solution with a concentration of 5.12 mg/mL.
(4) preparation of bacterial suspension: under sterile conditions, the experimental strains cultivated to the logarithmic growth phase were corrected to the 0.5 Mcfarland Standard with MHB medium, and diluted at a ratio of 1:200 for later use.
(5) determination of MIC by micro-double dilution method: a sterile 96-well plate was taken, 10 μL of moxifloxacin sample solution was added to the 2nd well, 10 μL of DMSO solution was added to the 4th-11th wells, 10 μL of the sample solution diluted by gradient was added to the 3rd and 4th wells, and the drug was subjected to double dilution until the 10th well, and the 11th well is the solvent control. Then 190 μL of diluted bacterial suspension was added to each well to make the final bacterial concentration of 5×10$^5$ CFU/mL in each well, and incubated in a constant temperature and humidity incubator at 37° C. for 20-22 h.

(6) MIC endpoint interpretation: the concentration at which the growth of bacteria can be completely inhibited as seen in the 96-well plate under the black background is the minimum inhibitory concentration of the sample against the bacteria. (Part of the in vitro antibacterial results of the representative compound 2 are shown in FIGS. 17-21)

TABLE 1

Minimum inhibitory concentration of the tested drugs (μg/mL)

| Compound | ATCC 12228 | ATCC 25923 | ATCC 29213 | ATCC 33591 | ATCC 14028 | ATCC 19606 | ATCC 25922 | CMCC 44103 |
|---|---|---|---|---|---|---|---|---|
| Retapamulin | 32 | 4 | 4 | 32 | 128 | 16 | 32 | 32 |
| Tiamulin | 16 | 64 | >128 | 128 | 128 | 64 | 128 | 64 |
| Valnemulin | 64 | 4 | 2 | >128 | 64 | 2 | 16 | 64 |
| 1 | 2 | 0.5 | 0.125 | 1 | 2 | 4 | 2 | 0.25 |
| 2 | 1 | 0.0625 | 0.0625 | 1 | 2 | 1 | 0.0625 | 0.5 |
| 3 | 1 | 1 | 0.25 | 2 | 2 | 2 | 1 | 2 |
| 4 | 1 | 0.5 | 0.5 | 1 | 0.5 | 2 | 0.5 | 1 |
| 5 | 2 | 32 | 2 | 2 | 4 | 8 | 2 | 32 |
| 6 | 2 | 0.5 | 0.25 | 1 | 2 | 2 | 2 | 2 |
| 7 | 2 | 0.5 | 0.125 | 1 | 2 | 2 | 1 | 0.5 |
| 8 | 8 | 1 | 0.125 | 64 | 32 | 32 | 2 | 8 |
| 9 | 2 | 1 | 1 | 2 | 1 | 16 | 2 | 1 |
| 10 | 2 | 2 | 0.125 | 2 | 2 | 2 | 0.5 | 1 |
| 11 | 2 | 1 | 0.5 | 2 | 4 | 2 | 2 | 0.5 |
| 12 | 2 | 1 | 0.5 | 2 | 2 | 2 | 1 | 1 |
| 13 | 128 | 64 | 128 | 64 | 16 | 8 | 32 | 32 |
| 14 | 64 | 64 | 128 | 64 | 16 | 8 | 32 | 8 |
| 15 | 32 | 128 | 64 | 64 | 16 | 8 | 16 | 32 |

From Table 1, compounds 1-15 have good inhibitory effects on *Staphylococcus epidermidis* (ATCC 12228) and *Staphylococcus aureus* (ATCC 25923 and ATCC 29213), and the effects of compounds 1-12 are far better than those of the marketed pleuromutilin antibiotics. Among them, the MIC value of compounds 1, 4, 6 and 7 against ATCC 25923 is 0.5 μg/mL, the MIC value of compounds 1, 7, 8 and 10 against ATCC 29213 is 0.125 μg/mL, the MIC of compound 2 against ATCC 25923 and ATCC 29213 is up to 0.0625 μg/mL, which is the best antibacterial effect among all the compounds. Synthesized compounds 1-15 can inhibit methicillin-resistant *Staphylococcus aureus* (ATCC 33591); compared to the three marketed pleuromutilin antibiotics, it is found that the antibacterial effects of compounds 1-7 and compounds 9-12 are better than the marketed drugs.

In addition, compounds 1-15 also show antibacterial activity against *Salmonella* (ATCC 14028) and *Acinetobacter baumannii* (ATCC 19606), all the compounds have MIC values between 0.5 μg/mL and 32 μg/mL. Among them, compound 4 has the best antibacterial effect against ATCC 14028 (MIC=0.5 μg/mL), compound 2 has the best antibacterial effect against ATCC 19606 (MIC=1 μg/mL). Synthesized compounds 1-15 also have varying degrees of inhibitory effects against *Escherichia coli* (ATCC 25922 and CMCC 44103), and the antibacterial effects are not weaker than the three marketed drugs. Among them, compound 2 has the best effect with MIC values of 0.0625 and 0.5 μg/mL, respectively.

In summary, the pleuromutilin derivative containing thiazole-pyridine benzyl quaternary ammonium salt side chain of the present invention can produce inhibitory effects against different bacterial strains, most of the compounds have stronger inhibitory ability against drug-resistant bacteria than the three marketed drugs, and have the significance of further clinical research.

TABLE 2

Minimum inhibitory concentration of the tested drugs against clinical drug-resistant bacteria (μg/mL)

| | | Compound | | |
|---|---|---|---|---|
| Strain | Retapamulin | 2 | 4 | 7 |
| MDR-PA 18-993 | 128 | 128 | 64 | 32 |
| MDR-PA 18-756 | >128 | 128 | >128 | 32 |
| MDR-PA 18-126 | 128 | 64 | 64 | 8 |
| MDR-KP 18-893 | 64 | 16 | 64 | 16 |
| MDR-KP 18-754 | 128 | 32 | 32 | 16 |
| MDR-KP 18-1482 | 64 | 64 | 64 | 16 |
| MRSA 18-171 | 128 | 4 | 16 | 64 |
| MRSA 18-209 | 128 | 128 | 128 | 16 |
| MRSA 18-575 | >128 | >128 | >128 | 64 |
| VRE 18-94 | >128 | >128 | >128 | 64 |
| VRE 18-80 | >128 | 2 | 2 | 8 |
| VRE 18-507 | >128 | >128 | >128 | 64 |
| CR-AB 18-184 | 128 | 16 | 64 | 32 |
| CR-AB 18-560 | 128 | >128 | >128 | 64 |
| CR-AB 18-882 | 64 | 8 | 8 | 16 |

It can be seen from Table 2 that compounds 2, 4 and 7 can produce different degrees of inhibitory effects against the 15 clinical drug-resistant bacteria tested, among which compound 7 has an inhibitory effect against all clinical drug-resistant bacteria better than that of retapamulin, has broad-spectrum antibacterial activity and is expected to become a new choice for clinical treatment of drug-resistant bacteria infection.

3. ANTI-MYCOPLASMA ACTIVITY ASSAY

The minimum inhibitory concentration of the pleuromutilin derivative containing thiazole-pyridine benzyl quaternary ammonium salt side chain against different mycoplasmas was tested with tiamulin as (purchased from Shanghai Yuanye Bio-Technology Co., Ltd) a positive control using a microbroth dilution method, and the antibacterial effect of the compound against different mycoplasmas was evaluated.

Experimental strains include *Mycoplasma hyopneumoniae* standard strain J strain (Mhp-J; NCTC 10110), *Mycoplasma hyopneumoniae* clinical isolate LH strain (Mhp-LH), *Mycoplasma hyorhini* standard strain BTS-7 strain (Mhr-BTS-7; NCTC 10130), *Mycoplasma gallisepticum* R strain (MG-R) and *Mycoplasma synoviae* WVU1853 strain (MS-WVU1853; NCTC 10124) (purchased from National Collection of Type Cultures, United Kingdom).

Figure 22:
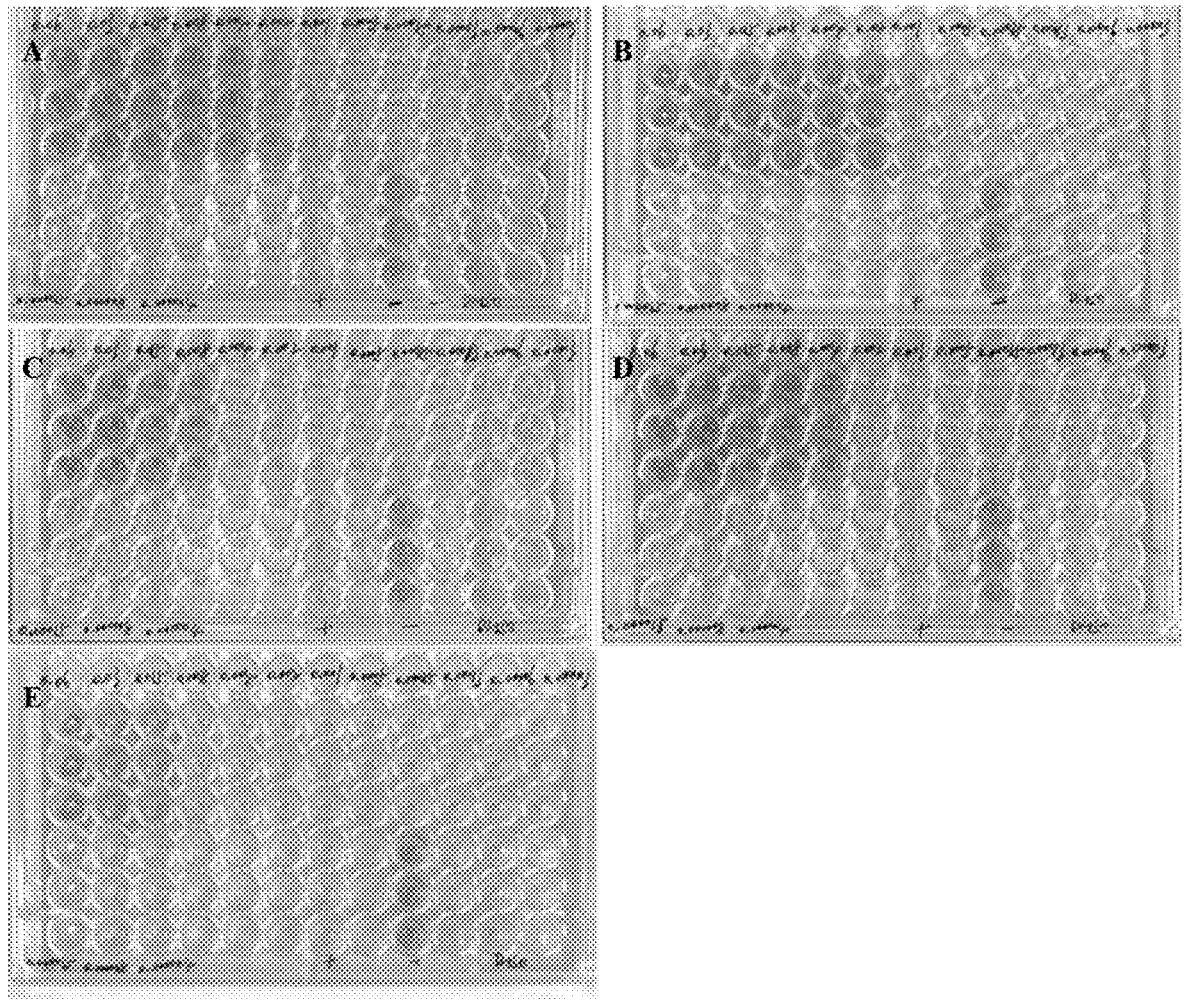
FIG. 22 is a graph showing the MIC determination results of compound 7 against 5 strains of *Mycoplasma*; wherein, (A) Mhp-J strain; (B) Mhp-LH strain; (C) Mhr-BTS-7 strain; (D) MG-R strain; and (E) MS-WVU1853 strain.

The specific operation steps are as follows:
(1) preparation of KM2 medium: 38.9 g of KM2 medium (purchased from Guangdong Huankai Microbial Sci. & Tech. Co., Ltd.) was weighed, added to 800 mL of distilled water, boiled and dissolved, and autoclaved at 115° C. for 20 min for later use.
(2) preparation of bacterial liquid stock: 0.5 mL of each of *Mycoplasma hyopneumoniae* (Mhp), *Mycoplasma hyorhina* (Mhr), *Mycoplasma gallisepticum* (MG) and *Mycoplasma synoviae* (MS) was taken and transferred to 4.5 mL of KM2 liquid medium, and when the colour of the medium turned yellow, each of the bacteria was sub-packaged at 0.5 mL per tube, and stored as the bacterial liquid at −70° C.
(3) determination of bacterial liquid titre (colour change unit, CCU): 96-well plate method was used to measure the bacterial liquid titre. The preserved bacterial liquid stock was taken from −70° C., melt and equilibrated to room temperature. 0.18 mL of KM2 medium was added to each well of the middle 4 rows of the 96-well plate (that is, 4 parallels), 0.02 mL of the bacterial liquid stock was taken and added to the wells of the first column, respectively, and subjected to 10-fold dilution until $10^{-11}$. A negative control containing only KM2 medium was set (column 12). The plate was sealed and put into an incubator at 37° C., and the results were observed day by day. The highest dilution at which the colour of the medium can change was the CCU/mL of the strain.
(4) determination of MIC: the minimum inhibitory concentration of the compound against mycoplasmas was determined by a microbroth dilution method. Each drug to be tested was prepared as a stock solution with a concentration of 2560 μg/mL, and each drug stock solution was 2-fold diluted with KM2 liquid medium, and the test concentration range was 0.015-128 μg/mL (large concentration gradient) and 0.000004-0.06 μg/mL (small concentration gradient). An appropriate amount of seed bacterial liquid was taken and diluted to $10^4$ CCU/mL serially according to its titre. Drugs of various dilutions were added sequentially to the 96-well plate, and then an equal amount of diluted bacterial liquid was added. 200 μL of diluted mycoplasma liquid was set as a positive control, 200 μL of KM2 liquid culture medium was set as a negative control, and a solvent control group (10 μL of drug solvent+190 μL of mycoplasma liquid) was also set. Three parallels were set for each experiment. After all the culture plates were sealed, they were allowed to culture at 37° C. and observed daily, and the final MIC values were recorded. (See FIG. 22 for the MIC determination results of the representative compound 7 against 5 mycoplasma strains)

TABLE 3

CCU determination results of 5 mycoplasma strains

| Strain Name | CCU result ($\log_{10}$CCU/mL) |
|---|---|
| Mhp-J | 8888 |
| Mhp-LH | 8888 |
| Mhr-BTS-7 | 8888 |
| MG-R | 8888 |
| MS-WVU1853 | 7778 |

TABLE 4

MIC determination results of the tested drugs against 5 mycoplasma strains

| | MIC (μg/mL) | | | | |
|---|---|---|---|---|---|
| Test drug | Mhp-J | Mhp-LH | Mhr-BTS-7 | MG-R | MS-WVU1853 |
| Tiamulin | 0.03 | 0.015 | 0.03 | 0.125 | 2 |
| 7 | 0.004 | 0.002 | 0.008 | 0.004 | 0.015 |

The results in Table 4 show that the MIC values of compound 7 against *Mycoplasma hyopneumoniae* J strain and *Mycoplasma gallisepticum* R strain are both 0.004 μg/mL, the MIC value of compound 7 against *Mycoplasma hyopneumoniae* clinical isolate LH strain is 0.002 μg/mL, the MIC value of compound 7 against *Mycoplasma hyorhinois* BTS-7 strain is 0.008 μg/mL, and the MIC value of compound 7 against *Mycoplasma synoviae* WVU1853 strain is 0.015 μg/mL. The effect is better than that of the marketed pleuromutilin antibiotics, thus compound 7 has the significance of further study.

4. DETERMINATION OF SOLUBILITY OF COMPOUNDS

Experimental method: representative compounds 2, 4 and 7 were selected for solubility determination, and retapamulin hydrochloride was used as a control. 1 mg of each sample was taken and quantitatively dissolved in a 10 mL volumetric flask, and the absorption peak area was measured by a high-performance liquid chromatography; then, the saturated solutions of the representative compounds 2, 4 and 7 and the control drug retapamulin were diluted 10-fold, and the absorption peak area was determined by HPLC; their respective solubility was obtained by calculating the absorption peak area.

The experimental instrument was Shimadzu LC-16, the chromatographic column was Hypersil C18 ODS (4.6×250 mm×5 μm), the flow rate was 1.0 mL/min, the detection wavelength was 300 nm, and the mobile phase was 0.05 mol/L of aqueous acetic acid solution:acetonitrile=30:70.

TABLE 5

Solubility of the representative compounds 2, 4 and 7 (mg/mL)

| Compound | pH = 7.0 water | pH = 1.5 aqueous hydrochloric acid solution | n-octanol |
|---|---|---|---|
| 2 | 2.02 | 2.76 | 13.24 |
| 4 | 2.32 | 3.12 | 11.87 |
| 7 | 2.54 | 3.45 | 11.32 |
| Retapamulin hydrochloride | 0.12 | 0.23 | 1.15 |

The test results in Table 5 show that the tested compounds have good solubility in neutral aqueous solution, aqueous hydrochloric acid solution simulating the pH=1.5 in human gastric acid environment and n-octanol, and have greatly improved fat solubility and water solubility compared with the control drug retapamulin hydrochloride. The solubility of the three tested compounds in aqueous solution is more than 2 mg/mL, and the solubility in n-octanol is more than 10 mg/mL. These good characteristics give these compounds the potential for further development.

The above content is only to illustrate the technical idea of the present invention, and cannot limit the protection scope of the present invention. Any changes made on the basis of the technical solution according to the technical idea proposed in the present invention fall into the protection scope of the claims of the present invention.

The invention claimed is:

1. A pleuromutilin derivative containing thiazole-pyridine benzyl quaternary ammonium salt side chain, characterized in that, the pleuromutilin derivative containing thiazole-pyridine benzyl quaternary ammonium salt side chain is a compound of general formula I or a pharmaceutically acceptable salt thereof:

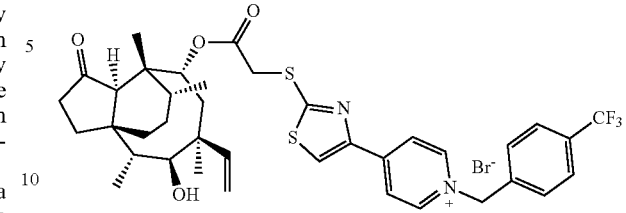

wherein, $R_1$, $R_2$ and $R_3$ are each independently selected from hydrogen atom, methyl, trifluoromethyl, methoxy, trifluoromethoxy, tert-butyl, nitro, cyano, halogen atom or phenyl.

2. The pleuromutilin derivative containing thiazole-pyridine benzyl quaternary ammonium salt side chain according to claim 1, characterized in that, a representative compound is selected from following compounds:

-continued

9
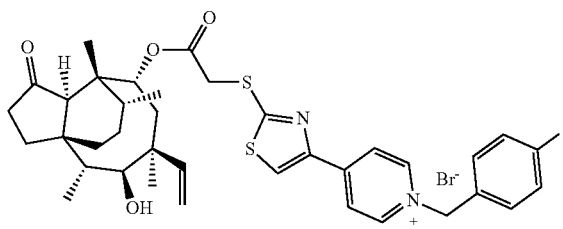

10
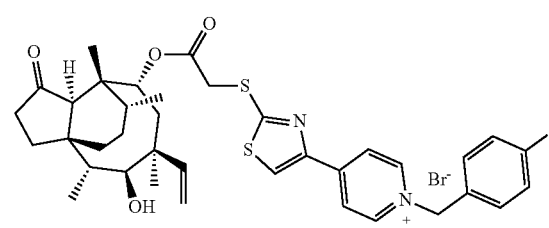

11
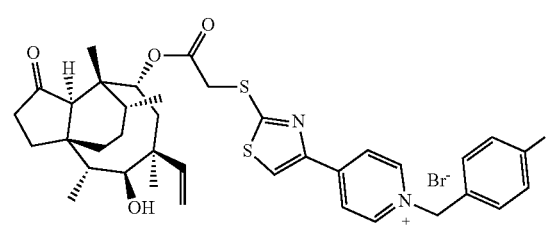

12
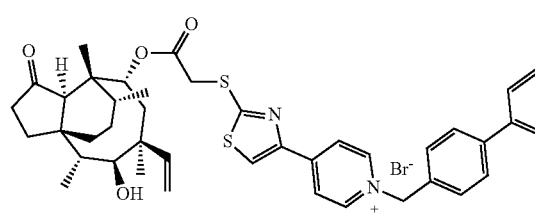

13
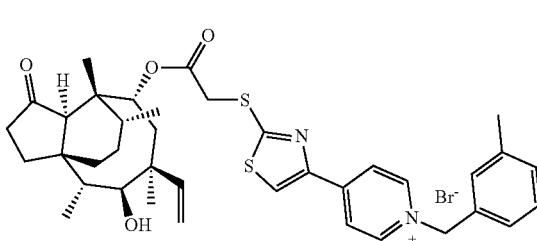

14
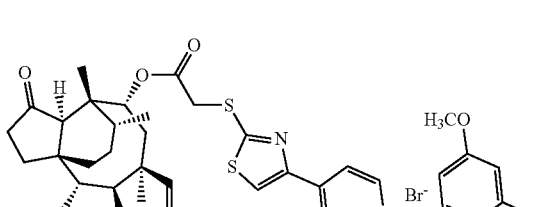

and

-continued

15
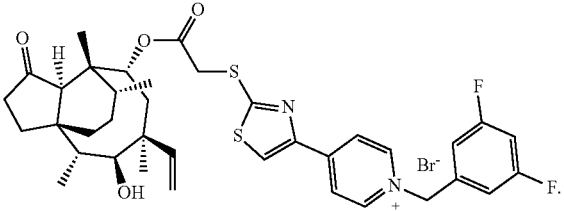

3. The pleuromutilin derivative containing thiazole-pyridine benzyl quaternary ammonium salt side chain according to claim 1, characterized in that, the pharmaceutically acceptable salt is a salt formed by the compound of general formula I and hydrochloric acid, hydrobromic acid, sulfuric acid, nitric acid, phosphoric acid, acetic acid, fumaric acid, maleic acid, oxalic acid, malonic acid, succinic acid, citric acid, malic acid, methanesulfonic acid, ethanesulfonic acid, benzenesulfonic acid, toluenesulfonic acid, glutamic acid or aspartic acid.

4. A method for preparing the pleuromutilin derivative containing thiazole-pyridine benzyl quaternary ammonium salt side chain according to claim 1, characterized in that, the method comprises the following steps:

1) A pleuromutilin is reacted with p-toluenesulfonyl chloride to obtain an intermediate I;
wherein, the intermediate I is

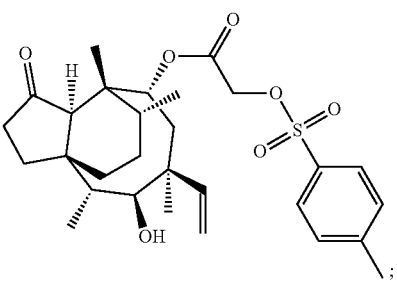 [SMILES: C=C[C@]1(C)C[C@@H](OC(=O)COS(=O)(=O)c2ccc(C)cc2)[C@]2(C)[C@H](C)CC[C@]3(CCC(=O)[C@H]32)[C@@H](C)[C@@H]1O]

2) The intermediate I prepared in step 1) and 2-mercapto-4-(4-pyridyl) thiazole are used as raw materials, dissolved in an organic solvent and reacted under catalyst catalysis and heating conditions, and an intermediate II is obtained after separation and purification;
wherein, the intermediate II is

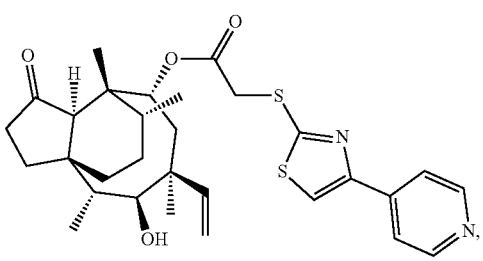 [SMILES: C=C[C@]1(C)C[C@@H](OC(=O)CSc2nc(-c3ccncc3)cs2)[C@]2(C)[C@H](C)CC[C@]3(CCC(=O)[C@H]32)[C@@H](C)[C@@H]1O]

and the catalyst is potassium carbonate and potassium iodide;

3) The intermediate II prepared in step 2) is used as a raw material, reacted with benzyl bromide compounds containing different substitutions, and after separation and purification, the pleuromutilin derivative containing thiazole-pyridine benzyl quaternary ammonium salt side chain with the structure shown in general formula I can be obtained.

5. The method for preparing the pleuromutilin derivative containing thiazole-pyridine benzyl quaternary ammonium salt side chain according to claim 4, characterized in that, in step 1), the molar ratio of the pleuromutilin to the p-toluenesulfonyl chloride is 1:1.2; in step 2), the molar ratio of the intermediate I to the 2-mercapto-4-(4-pyridyl) thiazole is 1:1.2; and in step 3), the molar ratio of the intermediate II to the benzyl bromide compounds with different substitutions is 1:2-6.

6. An antibiotic drug, characterized in that, the drug comprises an effective amount of the pleuromutilin derivative containing thiazole-pyridine benzyl quaternary ammonium salt side chain according to claim 1, and the balance is a pharmaceutical excipient.

* * * * *